(12) United States Patent
Garcia Reyes et al.

(10) Patent No.: US 11,304,844 B2
(45) Date of Patent: Apr. 19, 2022

(54) INTRA-ORAL DEVICE FOR MANDIBULAR ADJUSTMENT

(71) Applicant: Laboratorio Ortoplus, S.L., Malaga (ES)

(72) Inventors: Marcos Garcia Reyes, Malaga (ES); Juan Antonio Cabrera Carrillo, Malaga (ES); Alex Bataller Torras, Malaga (ES); Antonio Simon Mata, Malaga (ES); Jesus Garcia Urbano, Malaga (ES); Julio Moral Benicio, Malaga (ES); Ana Fernandez Guerrero, Malaga (ES)

(73) Assignee: Laboratorio Ortoplus, S.L., Malaga (ES)

( * ) Notice: Subject to any disclaimer, the term of this patent is extended or adjusted under 35 U.S.C. 154(b) by 119 days.

(21) Appl. No.: 16/619,252

(22) PCT Filed: Jun. 28, 2017

(86) PCT No.: PCT/IB2017/053855
§ 371 (c)(1),
(2) Date: Dec. 4, 2019

(87) PCT Pub. No.: WO2017/149523
PCT Pub. Date: Sep. 8, 2017

(65) Prior Publication Data
US 2020/0163795 A1    May 28, 2020

(30) Foreign Application Priority Data

Jun. 5, 2017 (EP) ..................................... 17382334

(51) Int. Cl.
*A61F 5/56* (2006.01)
*A61C 7/00* (2006.01)
*A61C 19/05* (2006.01)

(52) U.S. Cl.
CPC ................ *A61F 5/566* (2013.01); *A61F 5/56* (2013.01); *A61C 7/00* (2013.01); *A61C 19/05* (2013.01); *A61F 2005/563* (2013.01)

(58) Field of Classification Search
CPC .... A61F 5/566; A61F 5/56; A61F 5/58; A61F 2005/563; A61C 7/36; A61C 7/12;
(Continued)

(56) References Cited

U.S. PATENT DOCUMENTS

| 6,604,527 B1 | 8/2003 | Palmisano |
| 2010/0263676 A1 | 10/2010 | Thornton |

(Continued)

FOREIGN PATENT DOCUMENTS

| WO | 2014043817 A1 | 3/2014 |
| WO | 2016149742 A1 | 9/2016 |

*Primary Examiner* — Erin Deery
*Assistant Examiner* — Daniel A Miller
(74) *Attorney, Agent, or Firm* — The Webb Law Firm

(57) ABSTRACT

A device manufactured using CAD/CAM, including an upper splint (1) with followers (19) and various lower splints (2) including contact surfaces (3a) on which the followers (19) contact, so that on exchanging lower splints for others, according to a manufacturing sequence, they cause different controlled mandibular advancements. The contact surfaces (3a) reproduce a movement from the contact of the followers (19) on said contact surfaces (3a). The device is customised for each patient according to a set of anatomical parameters, and a series of input data measured by doctors, which personalise the device to achieve opening movement with single protrusive advancement in each of the lower splints (2).

11 Claims, 17 Drawing Sheets

(58) Field of Classification Search
CPC .... A61C 7/10; A61C 7/08; A61C 7/00; A61C 19/05; A63B 71/085
USPC .................. 128/848, 861, 846, 856, 859
See application file for complete search history.

(56) References Cited

U.S. PATENT DOCUMENTS

2016/0051398 A1\* 2/2016 Thornton ................ A61F 5/566
 128/848
2018/0147028 A1\* 5/2018 Warshawsky ............ A61C 7/36
2018/0153643 A1\* 6/2018 Lambert ................ A61F 5/566

\* cited by examiner

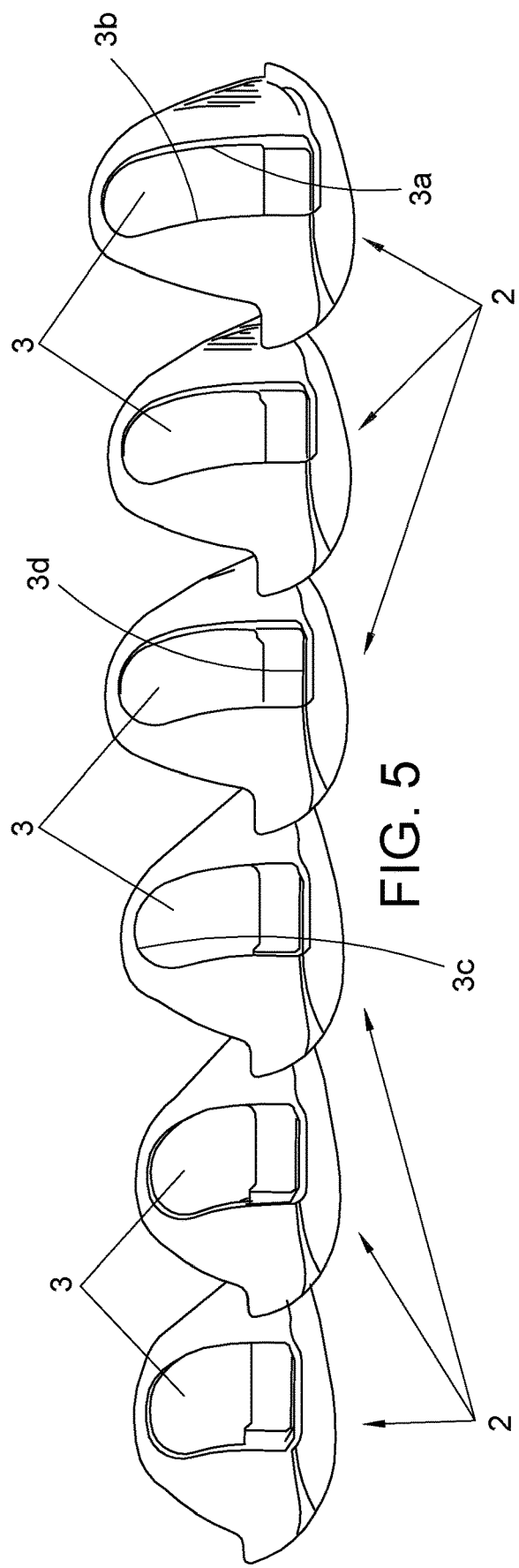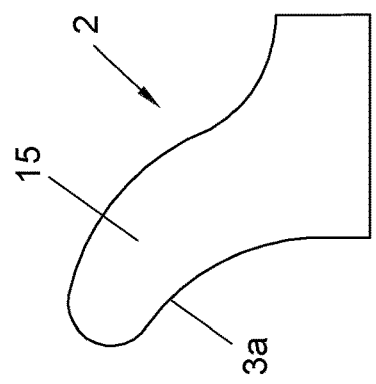

INTRA-ORAL DEVICE FOR MANDIBULAR ADJUSTMENT

CROSS-REFERENCE TO RELATED APPLICATIONS

This application is the United States national phase of International Application No. PCT/IB2017/053855 filed Jun. 28, 2017, and claims priority to European Patent Application No. 17382334.5 filed Jun. 5, 2017, the disclosures of which are hereby incorporated by reference in their entirety.

FIELD OF THE INVENTION

The present invention concerns an intra-oral device for mandibular adjustment, applicable in the treatment of sleep apnea, respiratory disorders and bruxism, as a sports mouth guard and as a positioner without set up (a device used to position the dental arches in an ideal position). The device includes an upper splint adapted to a patient's upper jaw and a lower splint adapted to a patient's lower jaw, wherein the upper splint and the lower splint are related to allow the positioning, in a customised and controlled way for each patient, of the lower jaw in different positions of protrusion advance, both when the patient's mouth is closed, when the mouth is open and during the process of opening and closing of the patient's mouth.

The device of the invention has the particularity of being totally customised for each patient, since splints are designed according to the patient's anatomy, oral cavity morphology, required mandibular protrusive advancement and the sequence, in millimetres, of the mandibular protrusive advancement that is desired, thus changing a lower splint for another lower splint with another different mandibular protrusive advancement.

The device of the invention falls within the technical sector of odontology for the design and manufacture of orthodontic devices, and more specifically for that of intra-oral dental appliances for the treatment of snoring, sleep apnea-hypopnea syndrome, as well as other disorders such as bruxism, breathing disorders, as a sports mouth guard, and a positioner without set-up.

BACKGROUND OF THE INVENTION

During peoples' sleep, the muscles relax causing the respiratory airways to close and vibrate on the passage of air. This vibration causes the sound known as snoring. Snoring, however, is not the only drawback of closure of the respiratory airways. This closure also causes a defective ventilation of the lungs, causing very poor sleep and even that the person stops breathing temporarily, this deficiency being known as sleep apnea.

Sleep apnea-hypopnea syndrome (SAHS) occurs when intermittent and repetitive obstruction of the upper airways occurs during sleep, due to collapse of the walls of the pharynx. Occlusion that occurs in the upper airways causes the complete interruption (apnea) or partial (hypopnea) airflow on inspiration.

During the night, the number of occlusions can vary from one to hundreds of times, depending on the severity of the disease, which causes that, over time, cardiovascular, cardiorespiratory, and cerebrovascular diseases, and neuropsychiatric disorders can be caused. These are the secondary effects due to oxygen desaturation, transient and subconscious awakenings caused by SAHS.

In addition, sleep apnea-hypopnea syndrome has a serious impact on patients' quality of life due to lack of sleep and/or deep sleep at night.

Currently, various intra-oral devices intended to act on a patient to reduce sleep apnea are known in the market. These intra-oral devices, known as MAD, advance the lower jaw relative to the upper jaw, opening a larger space in the back of the oral cavity and thereby facilitating the passage of air from the pharynx and also into the pharynx.

Intra-oral devices generally comprise a dental appliance made to measure for the patient with an upper splint intended to be placed in the upper dental arch of the upper jaw and a lower splint intended to be placed in the lower dental arch of the lower jaw. In a first embodiment, these two splints may be adhered to each other, called a monobloc device or apparatus, and in a second embodiment, the two splints comprise two independent elements. The intra-oral device of this second embodiment is the most commonly used at present.

Devices with separate parts typically connect the upper splint and the lower splint with mechanisms that are positioned and tensioned so as to maintain the lower splint forward relative to the upper splint, in comparison to a rest state in which both splints would be in a neutral position, one above the other, according to the normal bite of the patient.

Various types of mandibular advancement mechanisms are known in the state of the art. For example, central metal mechanisms composed of a lower part and an upper part, respectively connected to the lower splint and to the upper splint of the dental device, are known. The lower splint and the upper splint are interconnected by an adjustable mechanism in the longitudinal direction, for example by means of an adjustable threaded connection, which allows adjusting the position of the lower splint with respect to the upper splint. An example of this type of mandibular advancement mechanism is the patent with publication number DE 103 41 260. Another device with mandibular advancement mechanism is the Spanish patent with publication number ES 2 365 003 property of the same holder as the present invention.

This Spanish patent includes an adjustable central mechanism that adjusts the patient's mandibular protrusion. In addition, said adjustable central mechanism has a system that allows the patient to perform laterality, which are relative displacements in both directions of a transverse direction. In this way, the patient feels more comfortable and avoids problems in the dental arches. This device, described in the Spanish patent, allows opening and a simultaneous mandibular advancement during said opening.

These mandibular advancement devices based on metallic mechanisms have the drawback of being very rigid and uncomfortable for the patient, in addition to causing him/her a great visual impact.

Another type of mechanism is one that combines lateral metallic and acrylic elements. It comprises a device composed of a lower splint and an upper splint, which are connected laterally by upper and lower flanges, together with an adjustable screw in each of the upper flanges, which at the time of adjustment applies a force against the flanges causing the jaw to move forward. These described devices are represented by the product of Somnomed, Somnodent, which corresponds to that disclosed by the patent with publication number U.S. Pat. No. 6,604,527 and also in other products such as the dorsal application Dynflex, and that of Dr. Nordstrom, NorSor II produced by Murdock labs.

Alternatively, devices are known comprising mandibular advancement mechanisms made of plastic material, generally consisting of one or more plastic ties that link the lower splint and the upper splint of the device. In some cases, the mechanism is formed by a single tie arranged like a connecting rod in the front area of the upper and lower splints, interconnecting both so that the jaw is advanced with respect to the upper jaw.

In other cases, the mechanism consists of two ties, one on either side of the device, the ends of which are connected to one side of the lower splint and to the same side of the upper splint. An example of this mandibular advancement mechanism is disclosed in the patent with publication No. US 2012073582 A1 belonging to the Silent Nit device, or in the Narval device produced by Resmed as disclosed in the patent with publication No. 7146982.

In other cases, a single tie is provided, the ends of which are connected to two opposite sides of the lower splint and whose central area is supported on the front of the upper splint of the device. In general, devices provided with plastic mandibular advancement mechanisms are more comfortable for the patient because they have some lateral and/or longitudinal flexibility, which allows the patient to move the jaw slightly when they are asleep, while the jaw is kept correctly advanced with respect to the upper jaw, achieving greater comfort and adaptation in the patient.

The disadvantage of these devices is that they are very brittle and easy to break, besides being very uncomfortable when placing the plastic ties for the adjustment of the protrusion.

Finally, there is on the market a device which has solved some of the disadvantages of the former mandibular advancement devices, which consists of an upper splint and a lower splint, wherein the upper splint has one or more upper flanges, and the lower splint has one or more lower flanges, where the position of the lower and upper flanges are interchangeable so as to be able to adjust the patient's mandibular advancement.

This device, referred to in the previous paragraph, is digitally designed and manufactured by milling, which provides advancement precise increments to facilitate the calibration of mandibular advancement without the need for an adjustable mechanism or tie exchanges. Digital manufacturing also avoids production errors. This device is described in the patent with publication number US 2016/0184129, and is used by Microdental's Micro2.

The current limitations with the described mandibular advancement devices are as follows:
  Whether they are metal mechanisms or flanges, they have a unique structural design for all patients.
  They only take into account the structural design to perform the mandibular advancement, but this structural design is not projected into the cranial anatomy of the patients, there being a great variability in the cranial anatomy size and arrangement of the different anatomical parts that influence this disease.
  They do not take into account the changes in occlusion of the patient's mouth that occur with the use of the device used.

SUMMARY OF THE INVENTION

In order to achieve the objectives and avoid the drawbacks mentioned in the previous sections, the invention proposes an intra-oral mandibular adjustment device, comprising an upper splint configured to fit a patient's upper jaw and a lower splint configured to conform to the lower jaw of said patient, wherein the upper splint and the lower splint are related so as to be able to place the lower jaw in different positions when the patient makes use of the device of the invention.

In one embodiment of the invention, the intra-oral device comprises extensions, which in turn comprise two side contact surfaces and two side followers, and housings delimited by edges comprising contact surfaces, where the followers are located on the opposite sides of the upper splint or lower splint, and where the housings are located in extensions that are interdependent to the lower splint or upper splint.

In another embodiment of the invention, the device could include a single follower and a single contact surface. It is also noted that the extensions may comprise a structure without the housings, so that in these cases the contact surface comprises one of the edges of said extensions.

The followers are fitted into the housings, where the followers are in tangential contact with the contact surfaces during use of the device of the invention. These contact surfaces in combination with the followers when in tangential contact with said contact surfaces constitute means for guiding and positioning of the lower jaw if the patient opens or closes the mouth.

In a closed position of the patient's mouth (position in contact with the occlusal plane); the contact surfaces in combination with the followers when in tangential contact with said contact surfaces constitute a means of static positioning of the lower jaw.

The followers of the intra-oral device comprise lugs protruding outwardly with respect to opposite outer faces of the lower splint or upper splint, where the followers are located below or above a plane delimiting a lower or upper surface of the upper splint or lower splint, respectively, all depending on whether the contact surfaces and followers are located on the lower splint or the upper splint.

The upper splint and the lower splint are related by a coupling with lateral gaps, wherein said lateral gaps are delimited between the extensions, and portions of the opposite outer faces, and wherein said lateral gaps allow controlled lateral mobility in a transverse direction of the lower jaw towards two opposite sides of the lower jaw when the patient makes use of the device of the invention.

The extensions include inner faces and outer faces opposite the inner faces, wherein said outer faces comprise dome-shaped surfaces on which internal mucous membranes of the patient's cheeks can rest to prevent said internal mucous membranes from entering into the housings and thereby preventing injury to the patient, possible pinching of the mucous membranes in particular.

The followers of the intra-oral device include ends located within the housings without protruding outwardly with respect to the outer faces of the extensions. This feature also helps to prevent possible damage to the mucous membranes of the cheeks.

Each housing comprises a closed contour, which is formed by an upper stop, a lower stop, the contact surface on which the follower contacts, and an additional surface facing, and opposite said contact surface. The upper stop can constitute an element that delimits the maximum opening of the patient's mouth. In turn, the additional surface constitutes a stop to limit a possible inadequate mandibular advancement of the patient.

In one embodiment of the invention, the contact surfaces of the housings comprise a profile with arched trajectory. The contact surfaces will be designed in accordance to the patient's parameters, which will define a trajectory to follow.

Our reference point is initially located in an incisor of the maxilla, from which the space that each contact surface will occupy for that patient is taken into account and the followers are placed taking into account the contact with said surface contact.

The numerous possible trajectories of the contact surface are defined by a characteristic equation which will be described below in the section of the embodiment example of the invention, so that, in order to determine the trajectory of the contact surface, the previously known positions of a first point of the lower incisors of the lower jaw when said first point is located in a position with the mouth closed (position in contact with the occlusal plane) and in a position with the mouth open are related. An initial tangential contact of the follower with the contact surface is also taken as known datum when the patient has the mouth closed.

In a particular embodiment of the invention, the followers are fitted into the housings in a position in which said followers are in contact with the contact surfaces, with the upper stops and with the lower stops of the housings maintaining a static position of the lower splint with respect to the upper splint, wherein the thus configured intra-oral device maintains the lower jaw in a resting position with the patient's closed mouth blocking the mobility of the patient's lower jaw.

In one embodiment of the invention, the two lateral contact surfaces are contained in two asymmetrical planes, where said contact surfaces are defined by different curves. This embodiment of the invention is applicable to those patients who have a deformity or defect in the upper jaw, lower jaw, or even in the mandibular joint, so that in this situation when these patients open his/her mouths, there is an asymmetric opening where the variation of the separation between the upper and lower molars of one side (right) of the mouth is different from the variation of the separation between the upper and lower molars of the other side (left) of the patient's mouth.

Thus, the device of the invention has the purpose of solving the problems caused by snoring and apneas due to a poor passage of air through the pharynx, based essentially on causing the mandibular advancement in a controlled way, so that the lower jaw is forced to move progressively forward, pulling with it the tongue and soft tissues that can posturally block the pharynx. According to the mandibular advancement required for each patient, the lower splints will be exchanged. The device of the invention has the particularity of being totally customised for each patient, since the structure of the splints is designed according to the patient's anatomy, the morphology of the oral cavity, the required mandibular advancement and the sequence in millimetres of the mandibular advancement that is desired in order to go from one lower splint to another lower splint, thus varying the trajectory of the contact surface.

To facilitate a better understanding of this patent specification and forming an integral part of it, a set of figures is attached, wherein the object of the invention is represented in an illustrative and not limiting way.

BRIEF DESCRIPTION OF THE DRAWINGS

FIG. 5 shows a profile view of a customised set of lower splints, wherein a succession of housings is highlighted with contact surfaces that allow different degrees of opening of the patient's mouth, in accordance with different positions of protrusion advancement of the lower jaw when the device of the invention is used. These housings are placed in some extensions.

FIG. 6 shows a profile view of a part of a lower splint, which highlights an extension that has a shape of shark fin with a different configuration to the extensions of FIG. 5.

DESCRIPTION OF THE INVENTION

Figure 1:
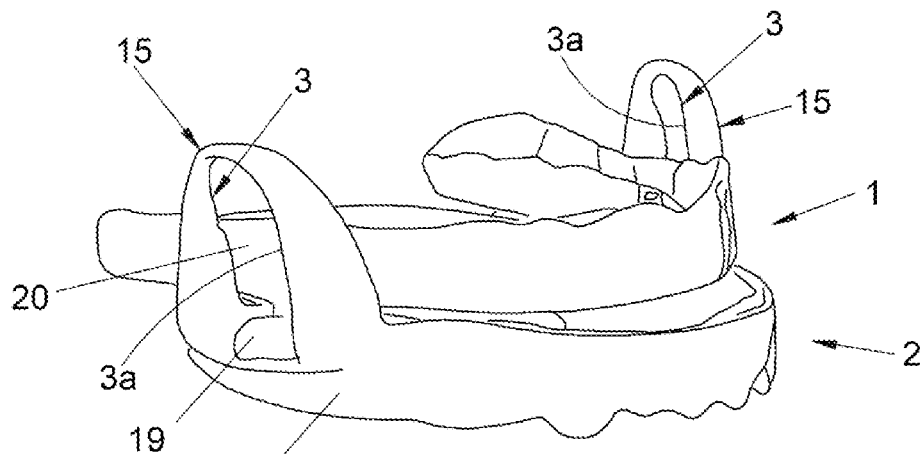
FIG. 1 shows a perspective view of the intra-oral device for mandibular adjustment, object of the invention. It comprises an upper splint and a lower splint related to each other.

Considering the numbering used in the figures, the intra-oral mandibular adjustment device comprises an arch-shaped upper splint (1) configured to be adapted and fixed to an upper jaw (16) of a patient and an arch-shaped lower splint (2) configured to be adapted and fixed to a lower jaw (9) of the patient.

The upper splint (1) and the lower splint (2) are related to each other to be able to place the lower jaw (9) in different controlled positions when the patient wearing the device of the invention has the mouth in the closed position, in the open position, and also during the movement of opening and closing of the mouth.

In one embodiment of the invention, the intra-oral device of the invention allows to place the lower jaw (9) with the mouth closed on an initial neutral position without retrusion and without protrusion advancement, while in other embodiments the intra-oral device allows to place the lower jaw (9) in different positions of mandibular advancement with the mouth closed.

On the other hand, during the opening of the patient's mouth, the intra-oral device generates intermediate positions in protrusion advancement of the lower jaw (9) which are more advanced positions than the initial position with the mouth closed. Including up to the maximum jaw opening that the device allows, the lower jaw (9) assumes a final position that is also a more advanced position than the initial position with the mouth closed and than all the intermediate positions that the lower jaw (9) runs along during its opening.

In a particular case, the intra-oral device of the invention maintains the initial mandibular advancement which is taken as an initial reference with the mouth closed, in all the intermediate positions and also the corresponding final position with maximum jaw opening that the device allow, i.e. in this particular case the intra-oral device of the invention maintains the initial mandibular advancement constant during the opening of the mouth and also when it reaches the final position corresponding with the maximum jaw opening that the device allows.

The intra-oral device shown in the figures comprises a pair of followers (19) arranged in a transverse direction (4) outside the molars of the patient's teeth, and at least one pair of contact surfaces (3a) also arranged outside the molars of the patient's teeth, where the followers (19) are configured to contact on said contact surfaces (3a) through a tangential contact. However, it is also possible that the device of the invention comprises a single follower (19) and a single contact surface (3a).

In the embodiments that are shown in the figures, the followers (19) are located on the upper splint (1) and the contact surfaces (3a) are located on the lower splint (2), although, it is also possible to do the reverse, i.e., that the followers (19) are located on the lower splint (2) and the contact surfaces (3a) are located on the upper splint (1).

Therefore, considering the embodiments shown in the figures, the intra-oral device comprises the two contact surfaces (3a) located on the lower splint (2), and two followers (19) located on the upper splint (1), wherein the followers (19) and contact surfaces (3a) are in correspondence with the molars of the upper jaw (16) and the molars of the lower jaw (9) of the patient, respectively.

The two followers (19) of the upper splint (1) are configured to be fitted into housings (3), wherein said housings (3) are located in extensions (15) interdependent to the lower splint (2), and where said housings (3) are delimited by edges that comprise the contact surfaces (3a) on which the followers (19) contact tangentially.

With this described structure and considering the embodiment shown in the figures, during the opening and closing of the mouth of a patient wearing the device of the invention, the lower splint (2) moves guided by the followers (19) of the upper splint (1) through the contact surfaces (3a) of the lower splint (2), where said followers (19) serve as fixed guiding elements on which the lower splint (2) is guided by tangential contact on the contact surfaces (3a) of the lower splint (2).

In the embodiment that is shown in the figures, each housing (3) of the lower splint (2) comprises a closed contour that consists of an upper stop (3c), a lower stop (3d) and two opposite faced guide sections called contact surface (3a) and an additional surface (3b), wherein said opposite guide sections of the contour of the housing (3) have arched profile trajectories.

In line with what was said in the previous paragraph, any position of the lower splint (2) depends on the tangential contact of the pair of followers (19) on the guide contact surfaces (3a) that define part of the contour of the housings (3) of the lower splint (2).

The two contact surfaces (3a) and the two followers (19) are configured so that a patient with the mouth closed in an initial resting position and when said patient is wearing the device of the invention on the inside of his/her mouth, his/her lower jaw (9) is placed, for example in a position of protrusion advancement, and that in any open mouth position of the user, the lower jaw (9) is placed in a position of protrusion advancement further forward than the initial position of protrusion advancement with the mouth closed, although it is also possible to maintain the initial position of protrusion advancement when the patient opens his/her mouth, as has already been referred to above.

According to the embodiment that is shown in the figures, the followers (19) of the upper splint (1) comprise lugs (19b) protruding outwardly with respect to opposite outer faces (20) of the lower splint (2), wherein the followers (19) are located below a plane (17) that delimits a lower surface of the upper splint (1). The lower splint (2) also includes opposite outer faces (20'). These opposite outer faces (20, 20') comprise outer side surfaces of the upper splint (1) and the lower splint (2).

On the other hand, when the upper splint is the part that includes the guide contact surfaces, and the lower splint is the piece, which includes the followers (19), in this embodiment not shown in the figures, the followers (19) will be located above a plane, which delimits an upper surface of the lower splint.

The coupling between the upper splint (1) and the lower splint (2) is a coupling with lateral gaps (18) that allow a controlled mobility of the lower jaw (9) towards both sides of the lower jaw (9) in a transverse direction to achieve greater comfort for the patient wearing the device of the invention within his/her mouth. The lateral gaps (18) are delimited between inner faces (15a) of the extensions (15) where the housings (3) are located, and some portions of the opposite outer faces (20) of the upper splint (1).

The extensions (15) include other outer faces (15b) opposite to the inner faces (15a), wherein said outer faces (15b) can contact with the internal mucous membranes of the cheeks of the patient, and where said outer faces (15b) comprise dome-shaped surfaces to better adapt to the patient's internal mucous membranes of the cheeks and more effectively prevent possible pinching of the internal mucous membranes of the cheeks in the areas of coupling of the followers (19) within the housings (3). These dome-shaped surfaces of the outer faces (15b) are configured taking into account, since they are customised, the shape of the dental arch of the patient.

Figure 2:
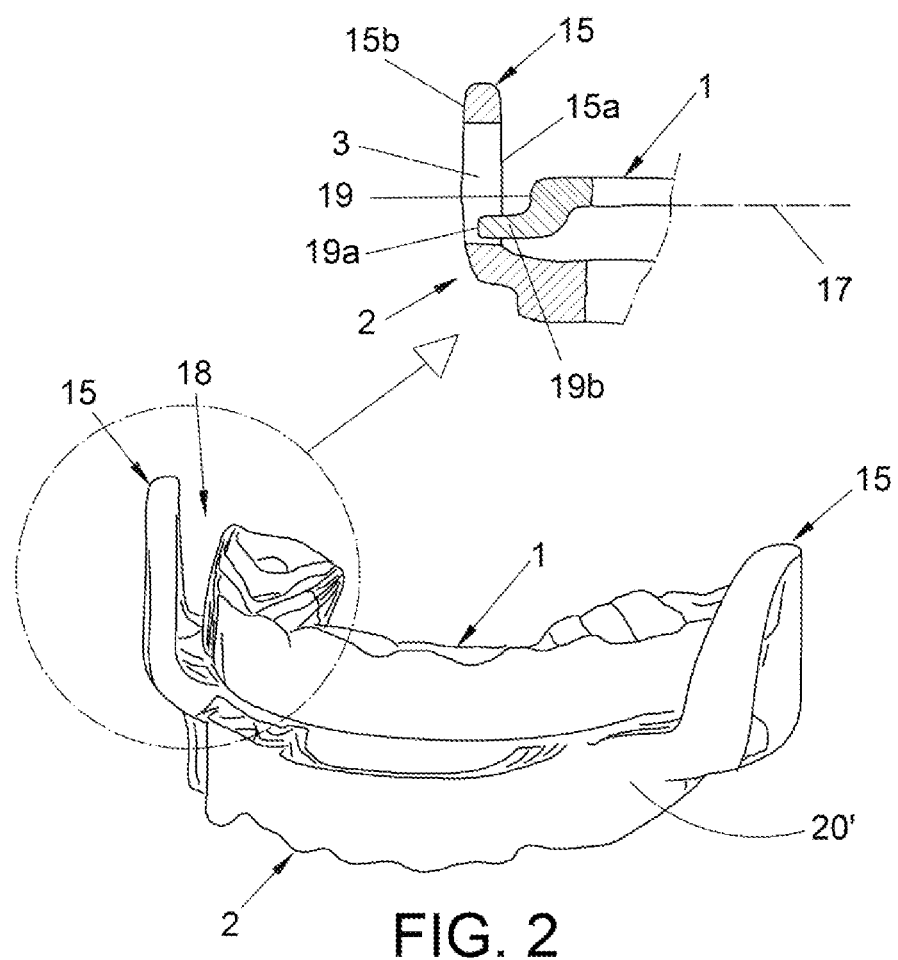
FIG. 2 shows another perspective view of the device of the invention.
Figure 3:
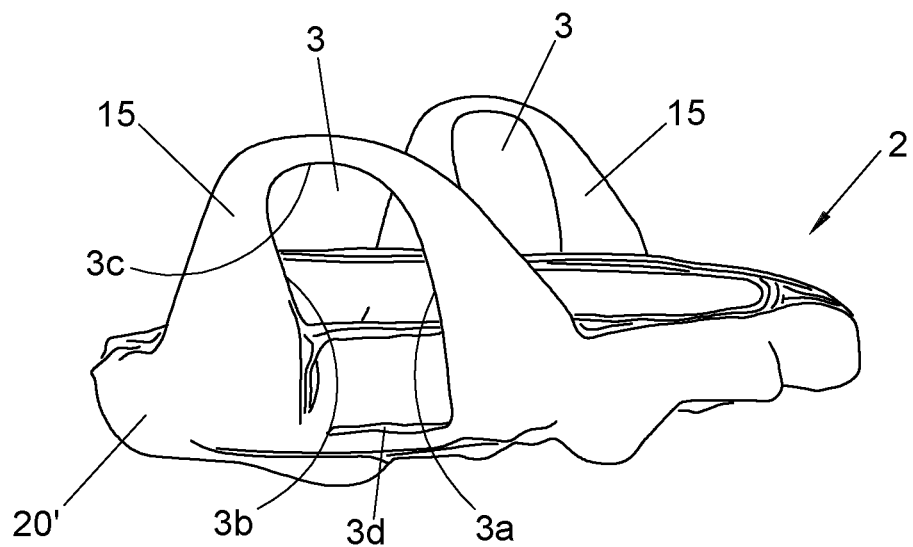
FIG. 3 shows a perspective view of the lower splint.
Figure 4:
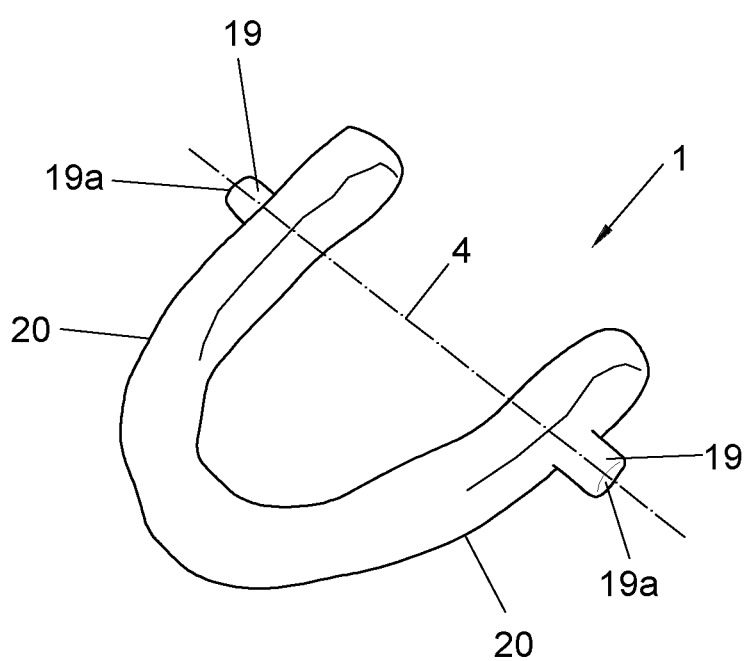
FIG. 4 shows a perspective view of the upper splint.

As shown more clearly in the detail of FIG. 2, the ends (19a) of the followers (19) are always maintained within the spaces of the housings (3) without protruding outwardly with respect to the outer faces (15b) of the extensions (15) of the lower splint (2).

In a first embodiment of the invention, the followers (19) of the upper splint (1) are located in a fixed position, while the contact surfaces (3a) of the lower splint (2) are located at a distance that may vary. In practice, an upper splint (1) and a set of several lower splints (2) are taken (FIG. 5), wherein the positioning of the extensions (15) and contact surfaces (3a) of the lower splints (2) varies from lower splints (2) with respect to other lower splints (2).

In a second embodiment, a particular lower splint (2) is taken maintaining a fixed positioning of the contact surfaces (3a), and a set of several upper splints (1) where the positioning of the followers (19) varies from the upper splints (1) with respect to other upper splints (1).

In a particular embodiment of the invention, the followers (19) of the upper splint (1) are fixed into the housings (3) of the lower splint (2), at the same time as said followers (19) are also in simultaneous contact with the contact surfaces (3a), the upper stops (3c) and lower stops (3d) of the housings (3) maintaining a static position of the lower splint (2) in the position desired with respect to the upper splint (1). In this way, the device keeps the lower jaw (9) in a resting position with the patient's mouth closed blocking the mobility of the lower jaw (9).

Figure 7A:
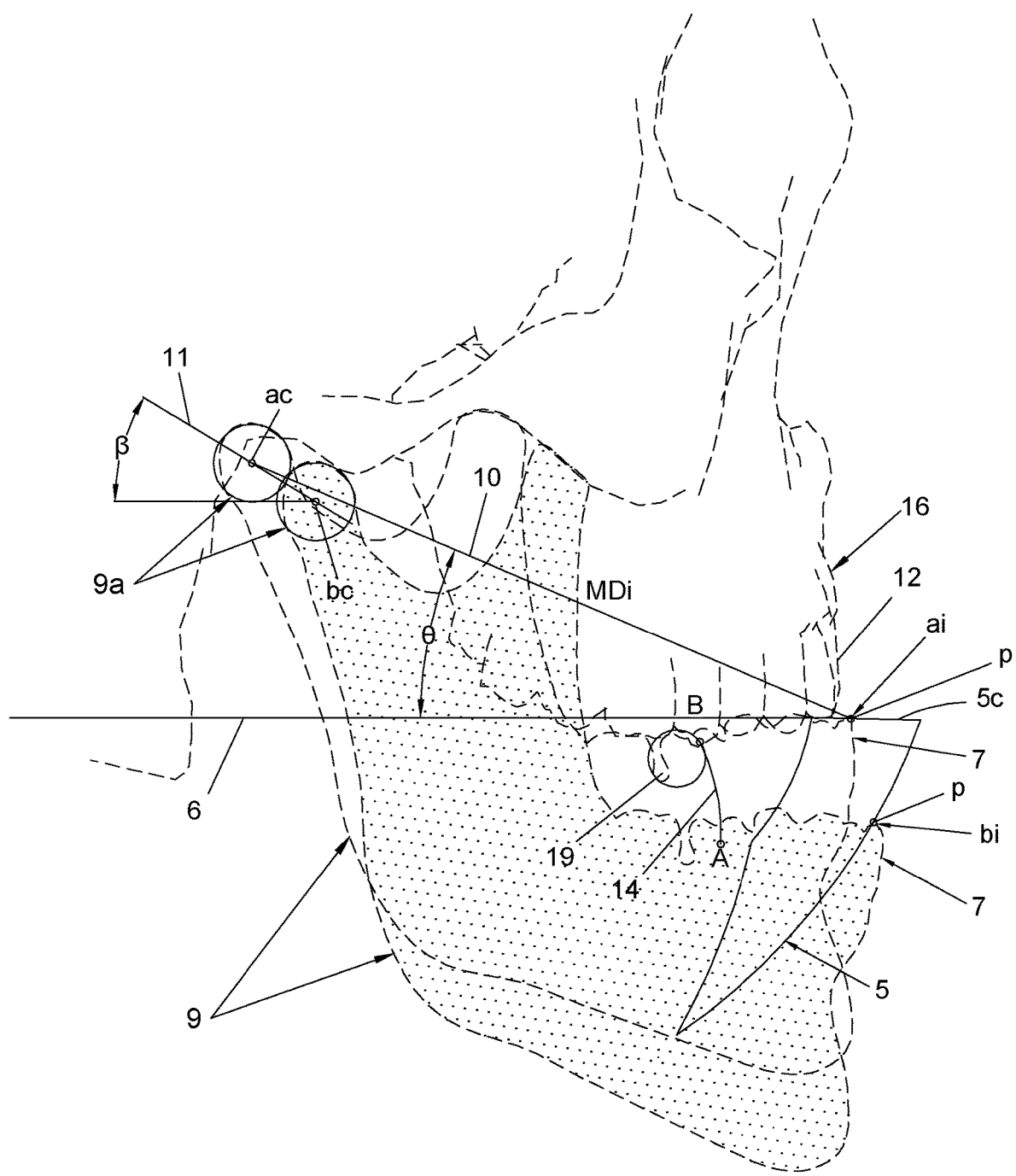
FIG. 7a represents a view mainly showing an initial position of a reference point of the lower incisors with a protrusion advancement of the lower jaw with the closed mouth of the patient (position in contact with the occlusal plane), and a final position of said point with the open mouth of the patient in its maximum opening, wherein said positions are at the limit edges of a Posselt diagram, and wherein said positions are conditioned by the invention device.

FIG. 7a shows a movement of the lower jaw, taking as a reference a point (p) of the central lower incisors (7) which passes from an initial position "ai" when the patient has his/her mouth closed with a determined percentage of protrusion advancement, up to a final position "bi" when the patient has his/her mouth open, also with a protrusion advancement further advanced than the initial position "ai" of protrusion with the mouth closed.

These positions: initial "ai" and final "bi" of the point (p) of the lower incisors (7) of the lower jaw (9) are located on the perimetral limits of a known Posselt diagram (5) represented by a surface delimited by a forward curved line (5a), a rear curved double line (5b) and an upper straight line (5c), the simplification of the patient's advancement movement corresponding to the straight line. This Posselt diagram (5) represents the pattern of limiting borderline movements of the lower incisors (7) of the lower jaw (9) with reference to the central point (p) of the central lower incisors (7) of the lower jaw (9).

The end limits of the upper straight line (5c) correspond to a point (c) of maximum retrusion and a point (d) of maximum protrusion of the lower jaw (9) when the mouth is closed, where said end limits correspond to the end positions of the point (p) of the lower incisors (7) of the lower jaw (9).

Figure 9:
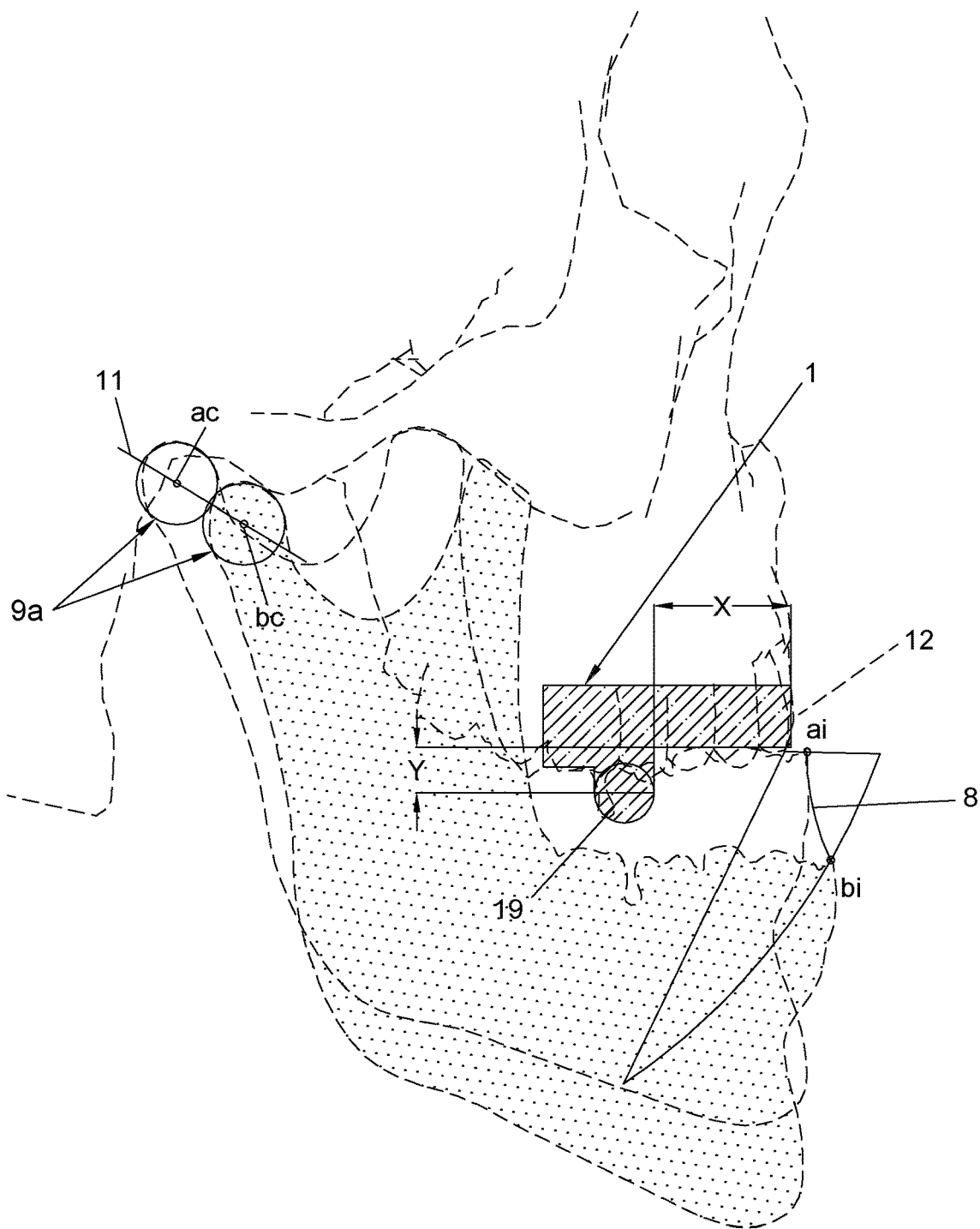
FIG. 9 represents a view wherein related distances measured in perpendicular directions with reference to a maxillary incisor tooth as point of origin are mainly shown. Specifically, they are distances measured between said point of origin and different positions of the tangential contact of followers of the upper splint with respect to the contact surfaces of the lower splint.

Thus, in said FIG. 7a the initial position "ai" of the point (p) of the lower incisors (7) is located in an area of the upper straight line (5c), and the final position "bi" of the point (p) of the lower incisors (7) is located on an area of the forward curve (5a). To reach these positions: initial "ai" and final "bi", the patient first moves his/her lower jaw (9) with the mouth closed until placing the point (p) of the incisors in one of the various initial positions "ai" with a determined degree or percentage of protrusion, (for example as shown in FIG. 9: (25%, 50%, 60%, 75%) and subsequently, with the initial position "ai" as reference, the patient opens his/her mouth until the point (p) of the incisors reaches the final position "bi" located on the forward curved line (5a), where the "b" final position is a position of protrusion advancement further forward than the initial position "ai".

The path from point (p) of the lower incisors (7) from the initial position "ai" to the final position "bi", is a path defined by a trailing edge (8), where it is possible to maintain the initial position of the mandibular protrusion advancement, and where said trailing edge (8) is performed during the mobility of the lower splint (2) dragged by the lower jaw (9), which moves following the trajectory of tangential contact of each contact surface (3a) on the follower (19).

The increase in the percentage of protrusion advancement of the lower jaw (9) with the mouth closed referenced with positions "ai" along the upper straight line (5c) (one of the multiple initial positions with other different percentages of protrusion advancement), is inversely proportional to the length of the trailing edge (8) which corresponds to the distance between each initial position "ai" of the point (p) of the lower incisors (7) which it takes along the upper straight line (5c) and each final position "bi" of the point (p) of the lower incisors (7) which it takes along the forward curved line (5a) of the Posselt diagram (5).

In this situation, taking, for example, a central point of the upper straight line (5c) of the Posselt diagram (5) as reference, the initial position "ai" would correspond to a percentage of protrusion advancement of 50%. As we approach the point (c) corresponding to the end of maximum retrusion, the percentage will decline, and as we approach the point (d) the percentage corresponding to the end of maximum protrusion will increase.

So, according to what is shown in FIG. 7a, in principle the point (p) located at the central point of the central lower incisors (7) of the lower jaw (9) is taken as reference; where from said point (p) of the lower incisors (7), a "MDi" mandibular dimension is measured which corresponds to a distance between the centre of the condyle (9a) and the point (p) of the central lower incisors (7) of the lower jaw (9).

A first angle "θ" is also measured to define the angular space between the plane of occlusion (6) where the upper straight line (5c) of the Posselt diagram (5) is contained and a first inclined straight line (10) that connects the centre of the condyle (9a) of the lower jaw (9) with the point (p) of the lower incisors (7).

An angle "α" is defined, which is an angular amplitude that corresponds to the rotation of the lower jaw (9) when the point (p) of the lower incisors (7) passes from the "ai" position to the "bi" position.

On the other hand, when the patient's mouth is closed with the lower jaw (9) in a position of protrusion advancement in which the point (p) of the lower incisors (7) is in the initial position "ai", the condyle (9a) takes a first referenced position with the point "ac", and when the patient opens his/her mouth up to point (p) of the incisors it passes from the initial position (ai) with the mouth closed to the final position "bi" with the mouth open, then the condyle (9a) takes a second position referenced with the point "bc" which is in a position further forward and below the point "ac"; in such a way that joining the point "ac" and the point "bc" a second inclined straight line (11) is obtained.

Between the second inclined straight line (11) and the occlusal plane (6) (parallel to the plane (17) that delimits the lower surface of the upper splint (1)) a second angle "β" is defined, which symbolises the direction in which the condyle (9a) will move during the opening of the mouth in a movement of protrusion advancement when the lower jaw (9) passes from the initial position "ai" to the final position "bi".

In the area of the lower incisors (7) the capacity of advancement of the lower jaw (9) is represented from the protrusion and retrusion data provided by the doctor and located on the upper straight line (5c), which correspond to the different initial positions "ai" of the point (p) of the lower incisors (7).

Once located the points of maximum protrusion and maximum retrusion of the condyle (9a), a curved line is drawn that simplifies the forward curved line (5a) and rear curved line (5b), since there is really only one curved line (distance between the condyle (9a) and the point (p) of the lower incisors (7) of the lower jaw (9)) centred on a point of the second inclined line (11), simplifying the displacement of the condyle (9a) and passing through the point (c) of maximum retrusion (rear curved line (5b)) and the point (d) of maximum protrusion (forward curved line (5a)).

The length of the rear curved line (5b) is around 20-25 mm of linear separation between an upper incisor (12) of the upper jaw (16) and the lower incisor (7) of the lower jaw (9), i.e. when the patient opens the mouth along the rear curved line (5b), a pure rotation is produced during the opening of the lower jaw (9) measured as a straight line between the lower incisors (7) and upper incisors (12) which reaches 20-25 mm. As occurs for the rear curved line (5b), the forward curved line (5a) is limited according to the data input for "maximum opening" of the patient's mouth and, therefore, of the lower jaw (9).

Figure 10:
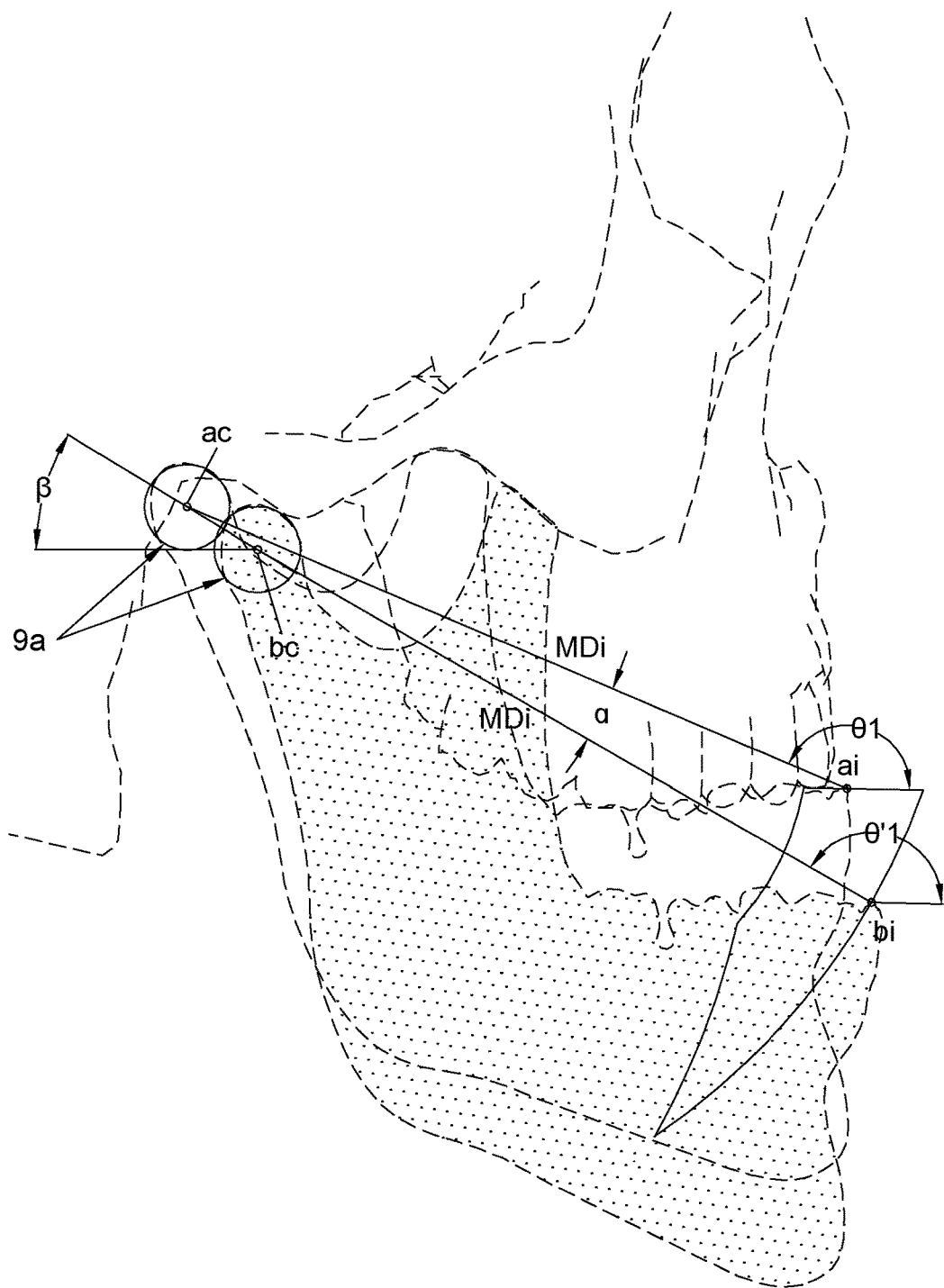
FIGS. 10-14b show a methodology used to define different curved trajectories that can be obtained with an equation, wherein said curved trajectories correspond to different contact surfaces.

FIG. 10 shows "X" and "Y" related distances measured in perpendicular directions with reference to a point of origin of the upper incisor (12) of the upper jaw (16). Specifically, they are distances measured between said point of origin and different positions that the followers (19) of the upper splint (1) may have, which are in contact with the contact surfaces (3a) of the lower splint.

This point of origin can be taken on an edge of the upper incisor (12) and also in other parts of said upper incisor (12). It could even be taken as a point of origin located on the upper splint (1) that may be in contact with the upper incisor (12).

Figure 7B:
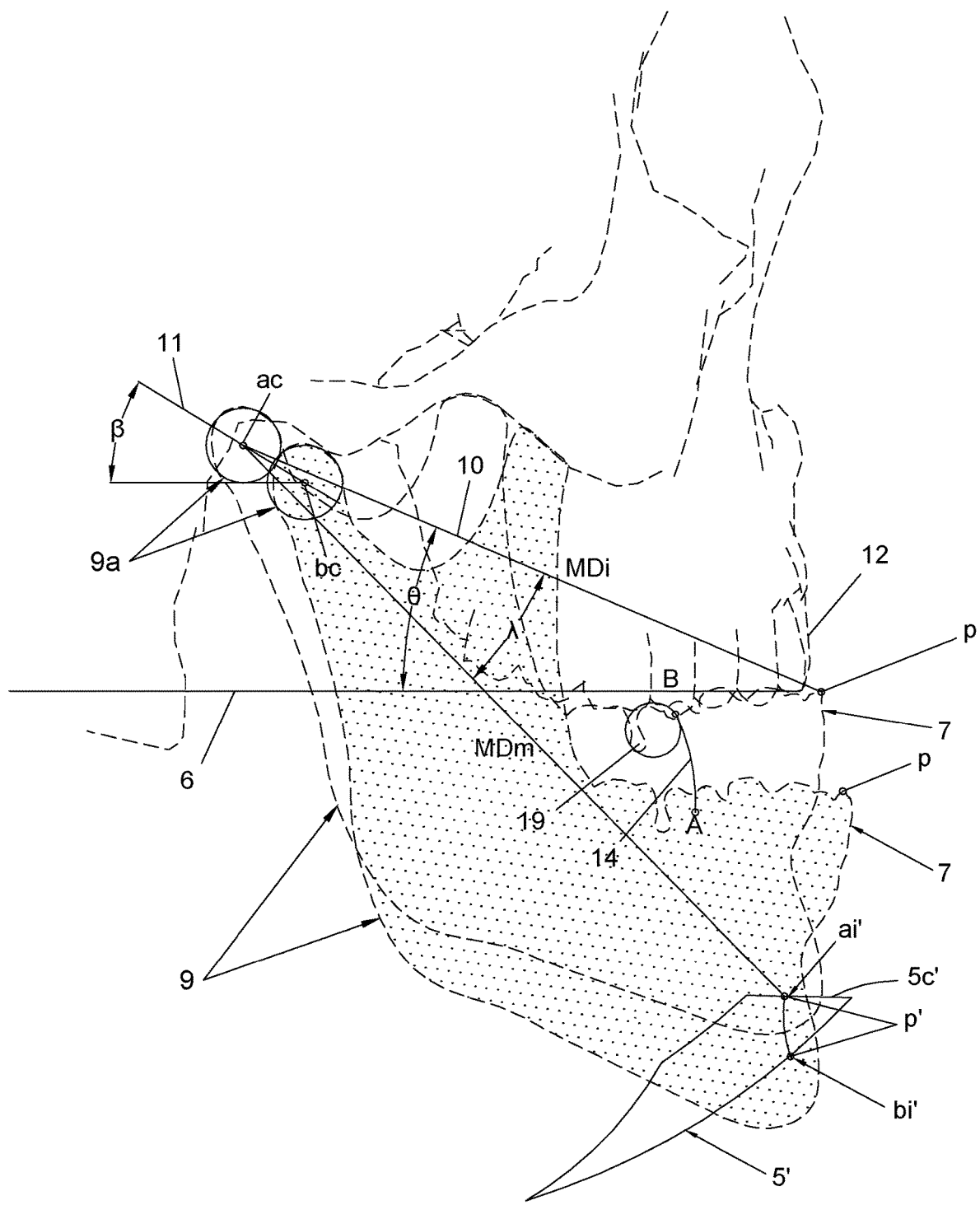
FIG. 7b shows a view similar to what is represented in FIG. 7a wherein, instead of taking as a reference point the incisors of the lower jaw, a central point is taken as a reference of the symphysis menti (Chin).
Figure 7C:
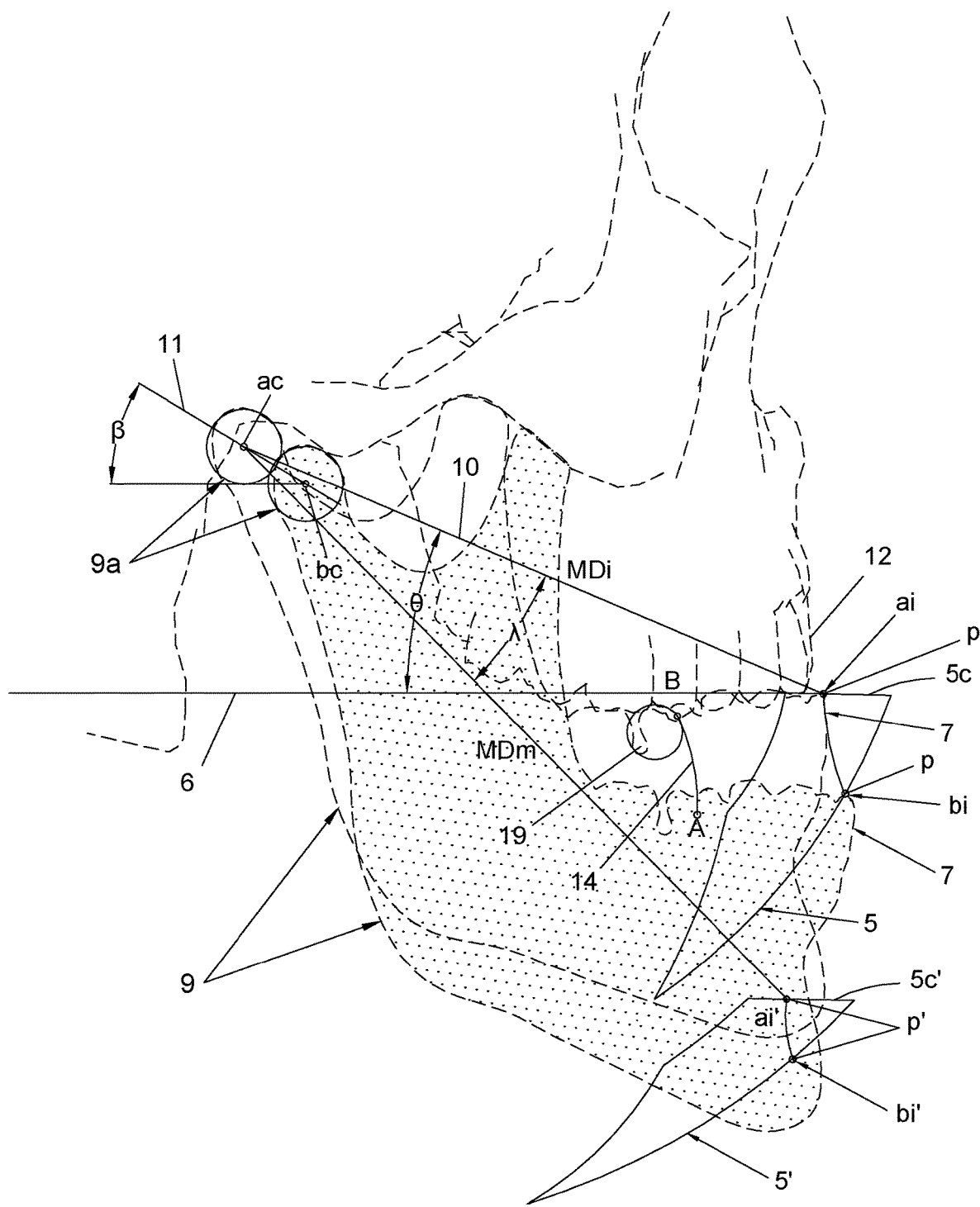
FIG. 7c represents a view that shows mainly an angular gap between the position of the reference point of the lower incisors and the position of the point of the symphysis menti.
Figure 8:
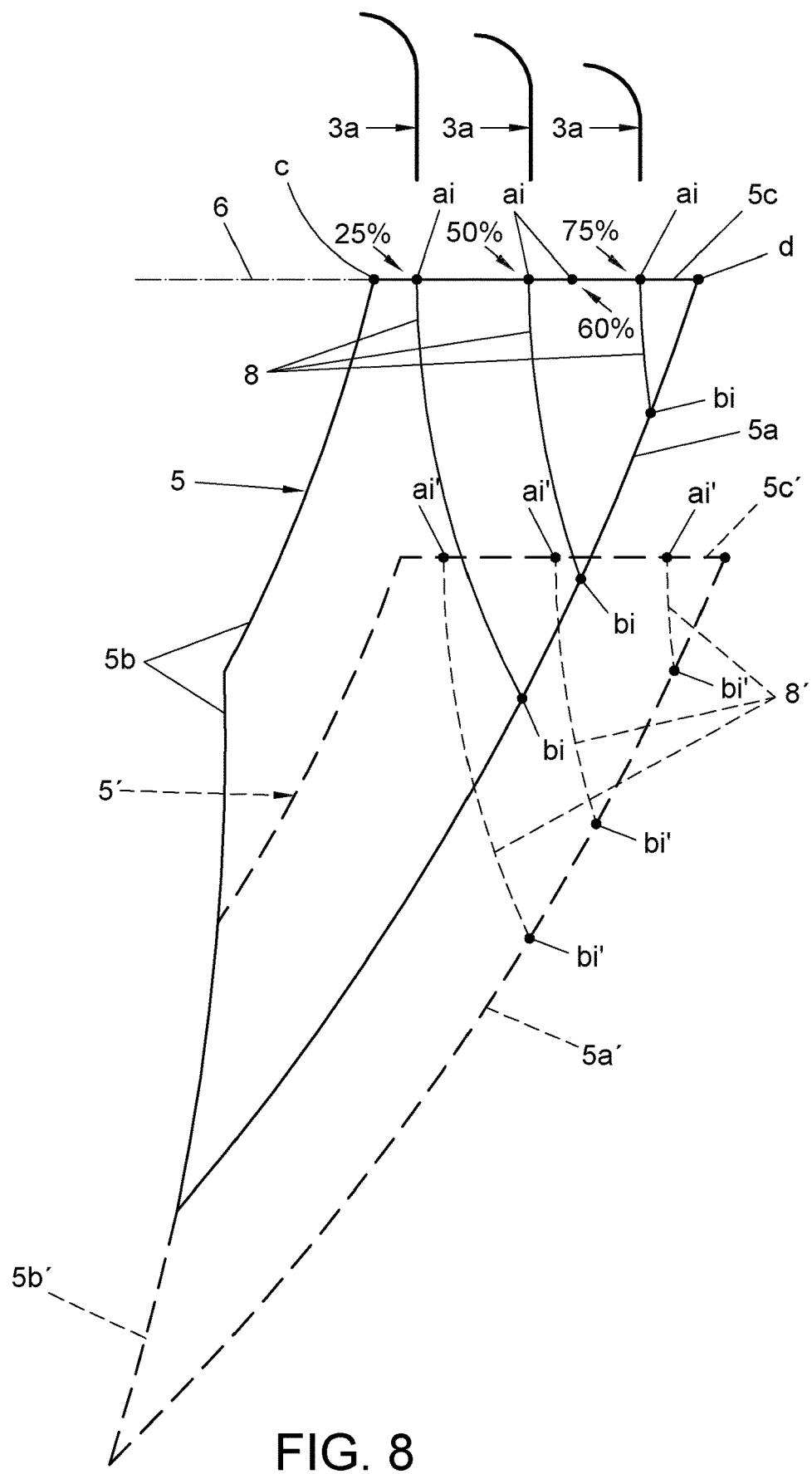
FIG. 8 shows a schematic view of a Posselt diagram, wherein several paths of the lower jaw dependent on the initial mandibular advancement with the mouth closed are highlighted, wherein the greater the initial mandibular advancement is, less is the path of the mouth opening from an initial position corresponding to said initial mandibular advancement to a final position corresponding with the maximum mouth opening.

In practice, as the lower jaw (9) is a single one-piece bone, it allows to directly obtain trailing edges (8') from the chin of the lower jaw (9) through different forms represented in FIGS. 7b, 7c and 8.

In terms of the methodology used, shown more clearly in FIGS. 7a, 7b and 7c, what is done is to calculate the trailing edge (8') with reference to a point (p') (located at the symphysis menti) of the chin from the trailing edge (8) of the lower incisors (7) with reference to a point (p) of said lower incisors (7) of the lower jaw (9); i.e., if we follow the trailing edge (8) of the lower incisors (7) the trailing edge (8') of the chin can be represented from a fixed mathematical structure as it is a triangle represented by a first segment "MDi", a second segment "MDm" and a third segment "ai'"-"ai" that is equal to the distance between the points (p-p') of the lower jaw (9); all as shown in FIG. 7c.

The first segment "MDi" is the distance between a position of protrusion advancement of the lower jaw (9) with reference to the initial position "ai" of the point (p) of the lower incisors (7) and the centre of the condyle (9a); the second segment "MDm" is the distance between the same advancement position of the lower jaw (9), but with reference to an initial position "ai'" of the point (p') of the chin; and the third segment is the distance between the positions of the points (p) and (p') of the lower incisors (7) and chin when they are taking their initial positions "ai" and "ai'", respectively.

However, to perform the representation, the whole configuration of the triangle formed is not needed, but actually only the first segment "MDi", the second segment "MDm" and an angle "λ" that forms both segments "MDi" and "MDm" are used.

From the range of total advancement (retrusion+protrusion) the doctor decides where to place a first model of lower splint (2) with specific contact surface (3a), which delimits part of the contour of the housing (3); for example 60% of the total advancement measured from the point (c) of maximum retrusion (FIG. 8); and therefore, the result is one of the initial positions "ai" represented (60%) of the point (p) of the lower incisors (7) with the mouth of the patient closed. This initial position (ai) will be located on the upper straight line (5c) of advancement of the Posselt diagram (5) and the final position "bi" of the point (p) of the lower incisors (7), where the mouth at the maximum opening will be located on the forward curved line (5a) of the Posselt diagram (5).

At the same time, with reference to the symphysis menti, the result is that the initial position "ai'" of advancement of the point (p') of the symphysis menti with the mouth of the patient closed will be located on the upper straight line (Sc') of advancement of the Posselt diagram (5') and a position "bi'" of the point (p') of the symphysis menti, where the mouth at the maximum opening will be located in the forward curved line (5a) of the Posselt diagram (5').

In line with what was said in the preceding two paragraphs, if we compare the position "ai" of the reference point (p) of the lower incisors (7) with respect to the initial position "ai'" of the point (p') of the symphysis of the chin; really said position "ai'" does not represent 60% of the advancement, but, when said initial position "ai'" is taken as reference, the advancement measured is greater than in the case of taking as reference the initial position "ai" of the lower incisors (7); all this as shown more clearly in FIG. 8.

The final position "bi'" of the point (p') of the symphysis menti depends on the mobility capacity of each patient, but as a minimum it is required to be in the same vertical as the initial position "ai'" of said point (p') when on the forward curved line (5a) of the Posselt diagram (5'). Therefore, the device of the invention does not generate a retrusion of the lower jaw (9), and also, obviously, no retrusion of the chin during opening of the mouth.

It is noted that the final position "bi" of the point (p) of the lower incisors (7) of the lower jaw (9) is calculated from the final position "bi'" of the point (p') of the chin.

The trailing edge (8') delimited between the "ai'", "bi'" positions of the point (p') of the chin is the curve by which it is decided to move the centre of the symphysis menti so that it does not retract and, in the case of the movement capacity of the lower jaw (9), it can even be advanced.

From said trailing edge (8'), the trailing edge (8) is delimited between the positions "ai", "bi" of the point (p) of the lower incisors (7) of the lower jaw (9).

The trailing edge (8), which traverses the point (p) of the lower incisors (7) from the initial position "ai" to the final position "bi", and the trailing edge (8'), which traverses the point (p') of the symphysis menti from the initial position "ai'" to the final position "bi'", are related to the contact surface (3a) of the lower splint (2) in the following way, according to FIGS. 7a, 7b, 7c, and 10.

Two important parts are considered:

Trailing edges (8, 8') of movement of the points (p, p') when they pass from the initial positions "ai"-"ai'" to the final positions "bi"-"bi'", respectively.

Position of each follower (19) of the upper splint (1) relative to the upper incisor (12) of the upper jaw (16). In the embodiment shown in the figures, said follower (19) is coupled to the upper splint (1), which in turn is fixed to the upper jaw (16), which is the fixed part, and with respect to which, the contact surface (3a) of the lower splint (2) will move.

With this described arrangement, when the movements corresponding to the trailing edges (8, 8') are made to pass, respectively, from the initial position "ai" to the final position "bi" (point (p)) of the lower incisors (7)), and from the initial position "ai'" to the final position "bi'" (point (p') of the chin)), a resulting curve (14) delimited between points "A" and "B" is generated due to each follower (19) being kept in a fixed position.

In this way, when the lower jaw (9) is occluded (mouth of the patient closed), the point (p) of the lower incisors (7) of the lower jaw (9) is in the initial position "ai", while the point (p') of the symphysis menti is in the initial position "ai'", and a first precise area of the contact surface (3a) of the lower splint (2) will be located in correspondence with the point "A".

In contrast, when the patient opens the mouth, the lower splint (2) is dragged by the lower jaw (9) and a movement corresponding to the resulting curve (14) is generated, where the point (p) of the incisors reaches the final position "bi", the point (p') located at the centre of the symphysis menti reaches the final position "bi'", a second precise area of the contact surface (3a) of the lower splint (2) will be located in correspondence with the point "B".

These calculations described can be performed in different ways whenever the reference points (p, p') of the lower incisors (7) or the symphysis menti of the lower jaw (9) are considered. In addition, any reference point can be taken from both the lower jaw (9) and the upper jaw (16), as any other cranial reference point. Other planes as a reference can also be taken such as the Frankfurt plane, Silla-Nasion plane and ENA-ENP plane. Other graphical and mathematical methodologies could also be used.

As for the calculations that refer to the point (p') of the symphysis menti, two main methodologies have been defined, although other methodologies can also be defined by taking as reference other points of the lower jaw (9).

The device of the invention is manufactured by CAD/CAM, wherein the various lower splints (2) are designed to increase the degree of advancement progressively to advance the lower mandible (2) millimetrically with the change of splints.

The linkage between the two splints: lower (1), upper (2), allows to perform a movement of opening and graduated advancement by means of the relative displacement of the contact surface (3a) of contact with respect to the follower (19), so that each contact surface (3a) of the upper splint reproduces a movement according to said contact surface (3a) by contact with the fixed element called the follower (19).

Each device of the invention has several lower splints (2) with two contact surfaces (3a) each, and the upper splint (1) with the two followers (19), wherein said contact surfaces (3a) change their shape, size and position according to a morphological study of the patient and various input data provided by the doctor such as: maximum opening of the patient's mouth, degree of mandibular advancement, degree of laterality and activation of the series of different contact surfaces (3a). The position, size and shape of the followers (19) can also be changed.

In this way, the different profiles of the contact surfaces (3a) are optimised for the patient's mandibular movement for each of the lower splints (2), allowing greater comfort, total freedom of movement and preventing the retrusion of the lower jaw (9). That is, each patient will have unique input data that will result in an individual device adapted to his/her anatomical characteristics.

The method for creating the sequence of splints comprises a succession of steps to be taken to obtain the different devices to achieve different mandibular advancements.

First, the profiles of the contact surface sequence (3a) are calculated with a mathematical model from a series of data that doctors measure in patients and from an anatomic-cranial study. The doctors' data are:
Retrusion measurement.
Maximum protrusion measurement.
Maximum opening measurement.
Initial degree of advancement of the sequence.
Activation of the step for the profile sequence of the contact surfaces (3a) on which the followers (19) contact.
As independent tasks, the doctor performs impressions of patients' dental arches.

These data serve as input to the mathematical model and to the neural network, which uses an anatomical study as a base, resulting in:
The mandibular dimension, defined as the distance between the central mandibular lower incisor (7) and the centre of the circumference of the condyle (9a).
The inclination of the occlusal plane (6) with respect to the Frankfurt plane.
The inclination of the second straight line (11), simplifying the condylar movement.
The inclination of the first inclined straight line (10) joining the lower incisor (7) to the upper position of the condyle (9a).
Mandibular dimension to the centre of the symphysis menti-condyle
Angle "λ" ("MDi"-"MDm").

The neural network will allow the continuous improvement of the device as the number of patients treated increases, so that the treatment of the future patients will start from a learning process that will allow to carry out adjustments on the device that will be able to increase, more and more, the efficiency and benefit of the therapy on the health of patients.

With all of the above information, an intra-oral device model is constructed which represents, for each patient, the curves of forward and trailing contact movements. These curves limit the trajectory that the jaw will make when the device of the invention is used, so that an opening movement with gradual protrusive advancement has been studied. From this curve and the points of the trajectory followed by the condyle (9a) through the joint cavity the profile of the contact surface (3a) required is obtained.

The opening achievable with the device of the invention is limited to a certain value because there may be patients in whom the upper airway section decreases as a consequence of the negative effect that the hyoid has on said section.

Through the activation data, which are the millimetres of mandibular advancement between the different steps of the splint sequences, the new curves of opening movements with protrusive advancement are calculated which will give rise to the new splints. The process continues until the maximum advancement permitted by the intra-oral device and the sequence of splints is generated with the step given, which will allow to re-adapt the treatment of the patient should he/she need more mandibular advancement. In this way, a treatment for the patient is formed by a set of splints with different contact surfaces (3a) that adapt to the patient's functional need at different points of advancement.

The exchanging from one to another splint of the intra-oral device can be customised as directed by the doctor.

In summary, each contact surface (3a) is individually and independently designed to control the advancement, degree of laterality and the possible three-dimensional rotations of the jaw.

The intra-oral device consists of two splints (1, 2) that will be manufactured from the digitisation of the impressions of both the patients' dental arches. From the set of designs of possible splints, the contact surface (3a) has been developed which, in at least one embodiment of the invention, has the upper stop (3c) which prevents opening in the case that the theoretical limit of the contour/trailing curves of the Posselt diagram is exceeded.

The structure of each extension (15), where the housing (3) is located, includes the outer face (15b) having a dome-shaped surface which acts as a resting surface for the mucous membranes of the inner face of the patient's cheek, preventing said mucous membranes from entering into the housing (3) through which the follower (19) can be displaced.

It is noted that preventing entry of the mucous membrane into the housing (3) through which the follower (19) is displaced is vital to prevent pinching and injury to the patient. It is also noted that the additional surface (3b) also has the function of side stop in case the patient performs mandibular advancement movements, where the follower (19) will contact with said additional surface (3b).

In one embodiment of the invention, the two lateral contact surfaces (3a) are contained in two symmetrical planes, wherein the device of the invention comprised in this embodiment is applicable to patients who, in principle, do not have deformities or defects in the upper jaw, lower jaw or mandibular joint, so that the opening of the mouth in these patients is normal without there being any asymmetries on either side of the mouth during opening.

In another embodiment of the invention, the two lateral contact surfaces (3a) are contained in two asymmetrical planes, wherein said contact surfaces (3a) are defined by different curves. This embodiment of the invention is applicable to those patients who have a deformity or defect in the upper jaw, lower jaw, or even in the mandibular joint, so that in this situation when these patients open his/her mouths, it is an asymmetric opening where the variation of the separation between the upper and lower molars of one side of the mouth is different from the variation of the separation between the upper and lower molars of the other side of the patient's mouth, so that the device of this embodiment is capable of respecting and maintaining the normal opening of the patient's mouth without causing tensions, maintaining said asymmetrical variation on both sides of the mouth during opening.

In line with what has been said in the previous paragraph, the mandibular rotation made by these patients with the design solution of the left and right side of the two contact surfaces (3a) is a unique design for each protrusion position according to the mandibular movement of the patient.

It should be noted that, in all cases, the curve of the trajectory of the curve of each contact surface (3a) has the ideal trajectory to reproduce the optimum mandibular trajectory (opening with advancement) of the Posselt diagram; it being also noted that the contact surface (3a) may have any design while maintaining tangential contact with the corresponding follower (19).

In addition, the device of the invention has the following characteristics to adapt it to the dental arch of each patient:

Adaptation of the contact surface (3a) and the follower (19) to the patient's dental arch. The design of said contact surface (3a) is made taking into account the inclination of the dental arch in the position of the follower (19) to reduce its impact upon insertion of the intra-oral device into the mouth.

The separation between the arch of the dental arch and the medial plane through the central upper incisors (12) of the upper jaw (16) is taken into account. These measures place the contact surfaces (3a) in their exact position and allow a certain degree of tolerance in the contact of the follower (19) and respective contact surface (3a). It is also a matter of achieving suitable movements of laterality according to the lateral gap (18) (FIG. 2).

Adaptation to the oral cavity. In order to adapt the intra-oral device to the oral cavity of each patient it is given an ergonomic shape, which has a longitudinal rounding depending on the depth to which the contact surface (3a) is placed with respect to the follower (19), and a transverse rounding depending on the height (dimension) of the contact surface (3a). In this way, the intra-oral device is adapted to the natural curvature of the oral cavity and is as comfortable as possible.

Cleaning. It does not have difficult access areas to a toothbrush.

Location of the contact surface (3a). In order to place the contact surface (3a) inside the lower splint (2), the retentive level of the teeth of each patient is studied and the points of maximum retention are located.

Vertical dimension. The dental arch of each patient is carefully studied to obtain the plane of occlusion that allows the movement of advancement and to have the smallest possible vertical dimension.

Moreover, it is noted that several studies have been carried out to develop a methodology that allows the trailing curves to be obtained and a customised intra-oral device being built to the morphological requirements of each patient, since the condylar kinematics, within the temporomandibular joint (TMJ), and the morphology of the dental arches of each patient are taken into account.

FIGS. 11 to 16 show how the "ICR" (instantaneous centre of rotation) methodology is carried out and also the numerous trajectories possible of the contact surface (3a) which is defined by a curve according to an equation, which is described below.

With this methodology, we can know the movement of any part of the lower jaw (9) from the known movement of a point of the same, in this case, the displacement of the lower incisors (7). In addition, if the extension (15) is in the lower splint (2), the points "al", "bl" which the contact surface (3a) of the extension (15) will have, can be determined from the positions "ai"-"bi" of the point (p) of the lower incisors (7), since said lower splint (2) will have an interdependent movement with the lower jaw (9). In the case that the extension (15) is in the upper splint (1), the points "al", "bl" of the contact surface (3a) of the extension (15) can be determined from the movement that the follower (19) will have, which will move interdependently to the lower jaw (9).

Each contact (3a) surface can also be incorporated into a fin-shaped extension (15) like the one shown in FIG. 6, wherein said contact surface (3a) is part of an outside edge that defines the fin-shaped extension (15).

Therefore, to determine the trajectory of the contact surface (3a), first of all it is necessary to calculate a final point "bl" of the contact surface (3a), which corresponds to the tangential contact of the follower (19) on the contact surface (3a); where the final point "bl" corresponds to an open position of the patient's mouth in which the point (p) of the lower incisors (7) of the lower jaw (9) is located in a final position "bi" in coincidence with the forward curve (5a) of the Posselt diagram (5).

For this, the localisation of an initial point "al" of the contact surface (3a) is taken as a basis, which corresponds to the tangential contact of the follower (19) on the contact surface (3a); where said initial point "al" corresponds to a closed position of the patient's mouth in which the point (p) of the lower incisors (7) of the lower jaw (9) is located in the initial position "ai" in coincidence with the upper line (5c) of the Posselt diagram (5).

During the opening of the patient's mouth, the position of the point (p) of the incisors will change along the contact curve (8) and as a result the centre of the condyle (9a) will also change position; for example from an initial position "ac" with the mouth closed to a final position "bc" with the mouth open.

The final position "bi" of the point "p" of the incisors with the mouth open can be any of the forward curve line (5a) that meets the condition of opening with advancement or that no retrusion is produced.

The "bc" position of the centre of the condyle (9a) is stable because the forward curved line (5a) is simplified with a circumference and, moreover, said position "bc" will be known thanks to the Posselt diagram (5).

In the device of the invention an advancement "s" of the condyle (9a) is calculated for each data of position "ai", "bi" of the point (p) of the lower incisors (7), unlike the device of the Somnodent patent (U.S. Pat. No. 6,604,527), wherein the displacement of the condyle is not taken into account for the calculation.

The angle "β" is a known fact because it is previously measured with an x-ray scanner, etc.

Therefore, the curved trajectory of the contact surface (3a) is defined by the following equation:

$$X = X_1 + X_2 + X_3 + X_4;$$

$$Y = Y_1 + Y_2 + Y_3 + Y_4;$$

wherein:

$$X_1 = x_{ai} \cdot (1-t)^3;$$

$$X_2 = 3 \cdot x_{i1} \cdot t \cdot (1-t)^2;$$

$$X_3 = 3 \cdot x_{i2} \cdot t^2 \cdot (1-t);$$

$$X_4 = x_{bi} \cdot t^3;$$

$$Y_1 = y_{ai} \cdot (1-t)^3;$$

$$Y_2 = 3 \cdot y_{i1} \cdot t \cdot (1-t)^2;$$

$$Y_3 = 3 \cdot y_{i2} \cdot t^2 \cdot (1-t);$$

$$Y_4 = y_{bi} \cdot t^3;$$

wherein:

$$x_{bi} = x_{ICR} + L_i \cos(\theta_4);$$

$$y_{bi} = y_{ICR} + L_i \sin(\theta_4);$$

al=$(x_{al}, y_{al})$=known input datum;
wherein:

$$L_i = \sqrt{(x_{al} - x_{ICR})^2 + (y_{al} - y_{ICR})^2};$$

$$x_{ICR} = x_{ai} + L_{ciri} \cdot \cos(\theta_i');$$

$$y_{ICR} = y_{ai} + L_{ciri} \cdot \sin(\theta_i');$$

$$\theta_4 = \theta_3 + \alpha;$$

wherein:

$$L_{ciri} = \frac{l_i}{\sin\left(\frac{\alpha}{2}\right)}$$

$$\theta_i' = \theta_i - 90 + \frac{\alpha}{2}$$

$$\theta_3 = \arctan\left(\frac{y_{ICR} - y_{al}}{x_{ICR} - x_{al}}\right)$$

wherein:
$l_i$=known lineal distance measured to the middle point of the straight line ai-bi;
$\theta_i$=known angle that forms the straight line ai-bi;
wherein:

$$\theta_i = \tan^{-1}\left(\frac{y_{bi} - y_{ai}}{x_{bi} - x_{ai}}\right)$$

α=angle of rotation of the jaw;
wherein:

$$\alpha = \theta_1 - \theta_1';$$

wherein:

$$x_{ai} + MDi \cdot \cos(\theta_1) = x_{bi} + x_{bc} + s \cdot \cos(\beta);$$

$$y_{ai} + MDi \cdot \sin(\theta_1) = y_{bi} + y_{bc} + s \cdot \sin(\beta);$$

$\theta_1$ and s are obtained;
wherein:
ai=$(x_{ai}, y_{ai})$=known input datum;
bi=$(x_{bi}, y_{bi})$=known input datum;
bc=$(x_{bc}, y_{bc})$=known datum;
MDi=mandibular distance known;
β=known angle;
wherein:
the variable "t" is delimited between 0 and 1;
the coordinates "$x_{al}$", "$y_{al}$" define an initial point "al" of the contact surface (3a) corresponding to a known initial position of the follower (19) when the mouth of the patient is closed;
the coordinates "$x_{bl}$", "$y_{bl}$" define a final point "bl" of the contact surface (3a) which corresponds to a final position of the follower (19) with the patient's mouth open;
the variables "$x_{i1}$", "$x_{i2}$" have a value delimited between the coordinates "$x_{al}$" and "$x_{bl}$"; and the variables "$y_{i1}$", "$y_{i2}$" have a value delimited between the coordinates "$y_{al}$" and "$y_{bl}$";
"ICR" is a point corresponding to an instantaneous centre of rotation of the lower jaw (9);
"$L_i$" is the distance between the point "ICR" and the initial point "al" of the contact surface (3a);
"$L_i$" is also the distance between the point "ICR" and the final point "bl" of the contact surface (3a);
"$L_{ciri}$" is the distance between the point "ICR" and a position "ai" of a point (p) of the lower incisors (7) of the lower jaw (9) with the mouth closed;
the angle "$\theta_4$" comprises a delimited angular space between a plane parallel to the plane of occlusion (6) with the mouth of the patient closed, and a direction passing through the point "ICR" and the final point "bl" of the contact surface (3a);
the angle "$\theta_3$" comprises a delimited angular space between a plane parallel to the plane of occlusion (6) with the mouth of the patient closed, and a direction passing through the point "ICR" and the initial point "al" of the contact surface (3a);

the angle "θ'$_i$" comprises an angular space delimited between the plane of occlusion (6) with the mouth of the patient closed and a direction passing through the point "ICR" and the position "ai" of the point (p) of the lower incisors (7) of the lower jaw (9) with the mouth of the patient closed;

the angle "θ$_i$" comprises an angular space delimited between the plane of occlusion (6) with the mouth of the patient closed, and a direction passing through position "ai" of the point (p) of the lower incisors (7) of the lower jaw (9) with the mouth closed and through a position "bi" of the point (p) of the lower incisors (7) of the lower jaw (9) when the mouth of the patient is open;

the angle "α" comprises an angular space delimited between a first direction passing through the position "ai" of the point (p) of the lower incisors (7) of the lower jaw (9) and an initial point "ac" of the condyle (9a) with the mouth of the patient closed, and a second direction passing through said point "ac" and a final point "bc" of the condyle (9a) with the mouth of the patient open; wherein the angle "α" is an angular amplitude corresponding to the rotation of the lower jaw (9) when the point (p) of the lower incisors (7) passes from the position "ai" to the position "bi";

the angle "β" comprises a delimited angular space between a plane parallel to the plane of occlusion (6) with the mouth of the patient closed, and a direction passing through the initial point "ac" of the condyle (9a) with the mouth closed and through the final point "bc" of the condyle (9a) with the mouth open;

the "s" distance is a distance delimited between the initial point "ac" of the condyle (9a) with the mouth closed and the final point "bc" of the condyle (9a) with the patient's mouth open;

"MDi" is the distance between the centre of the condyle (9a) and the point (p) of the lower incisors (7) of the lower jaw (9).

Figure 11:
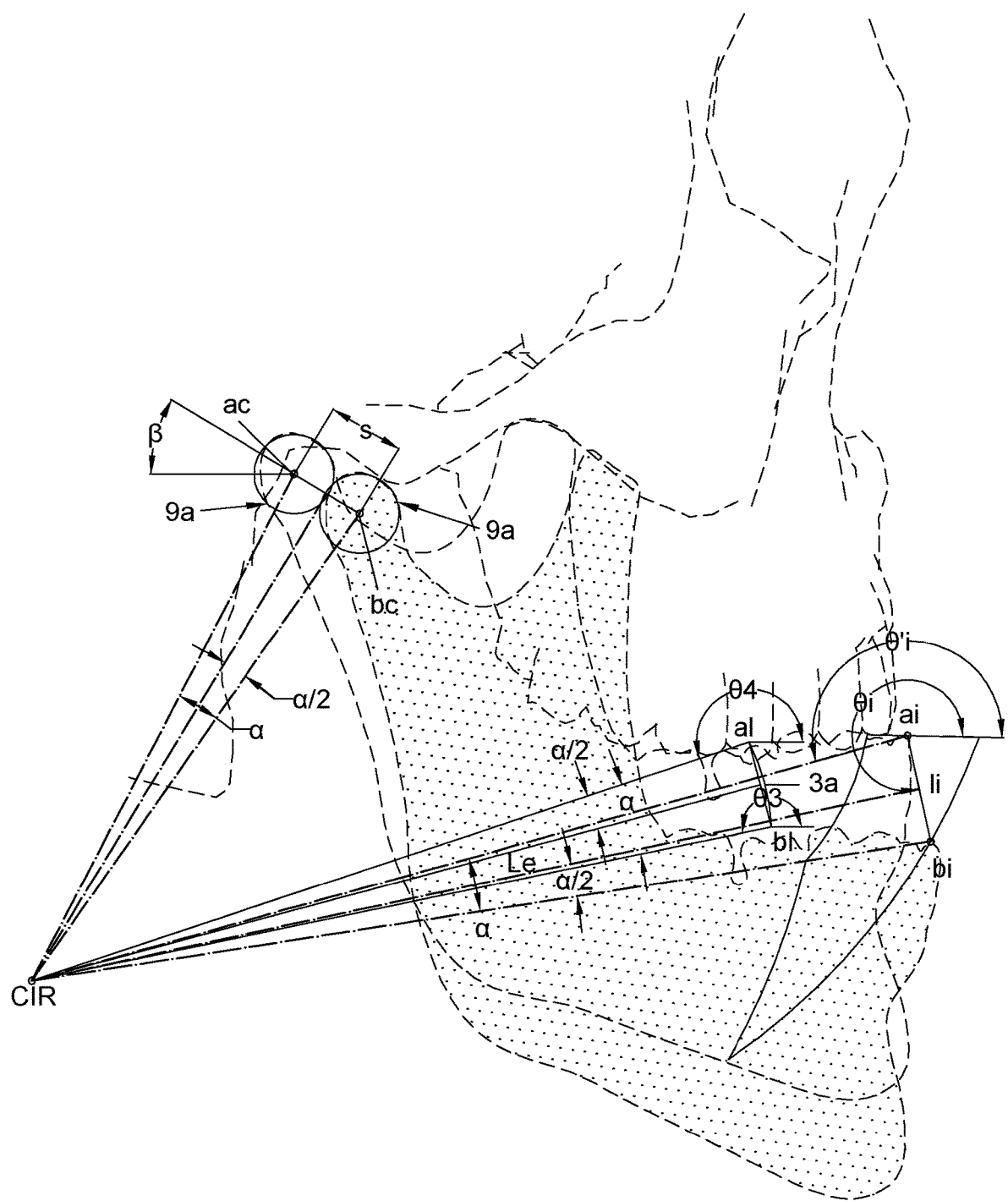
Figure 11A:
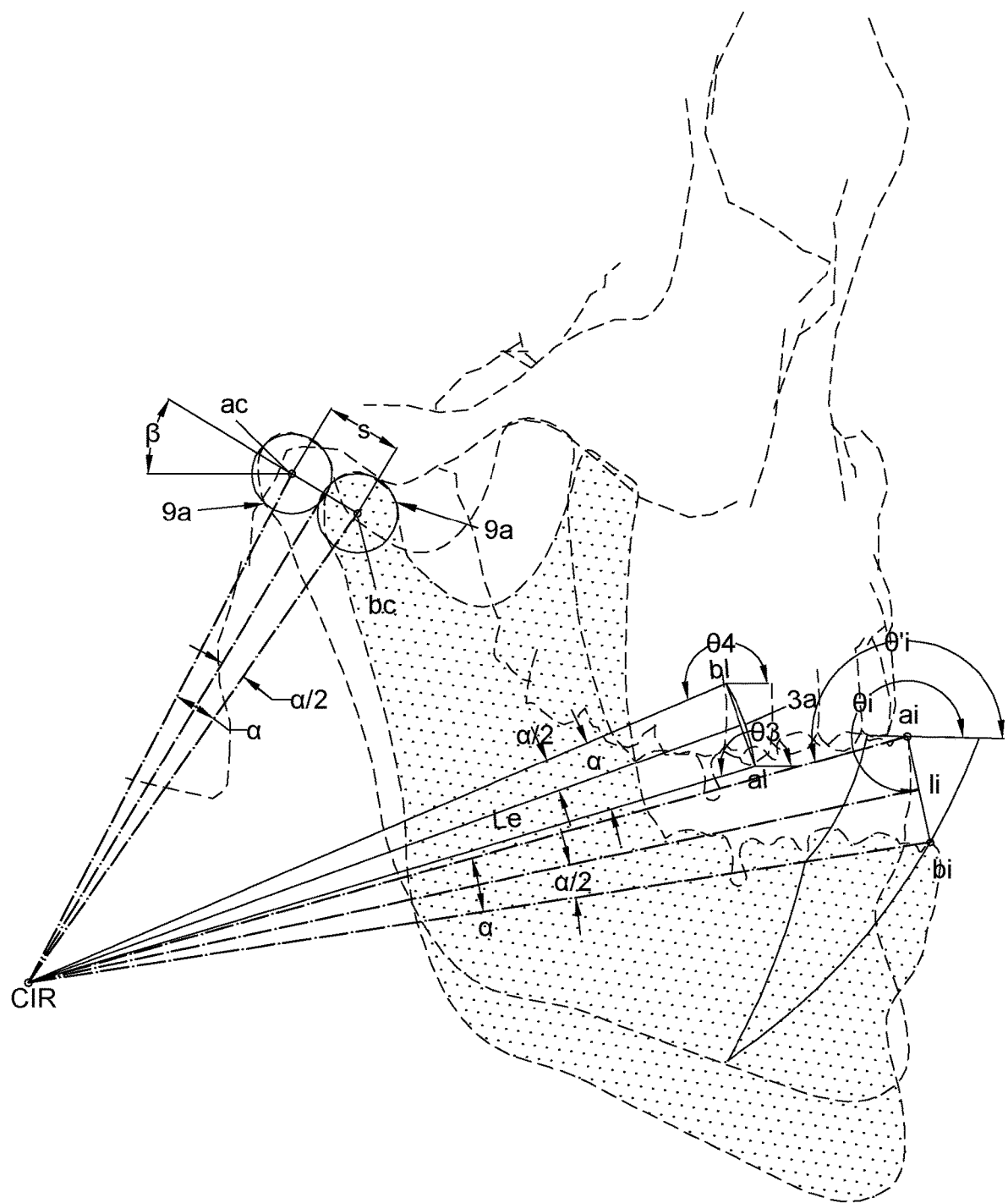
Figure 12:
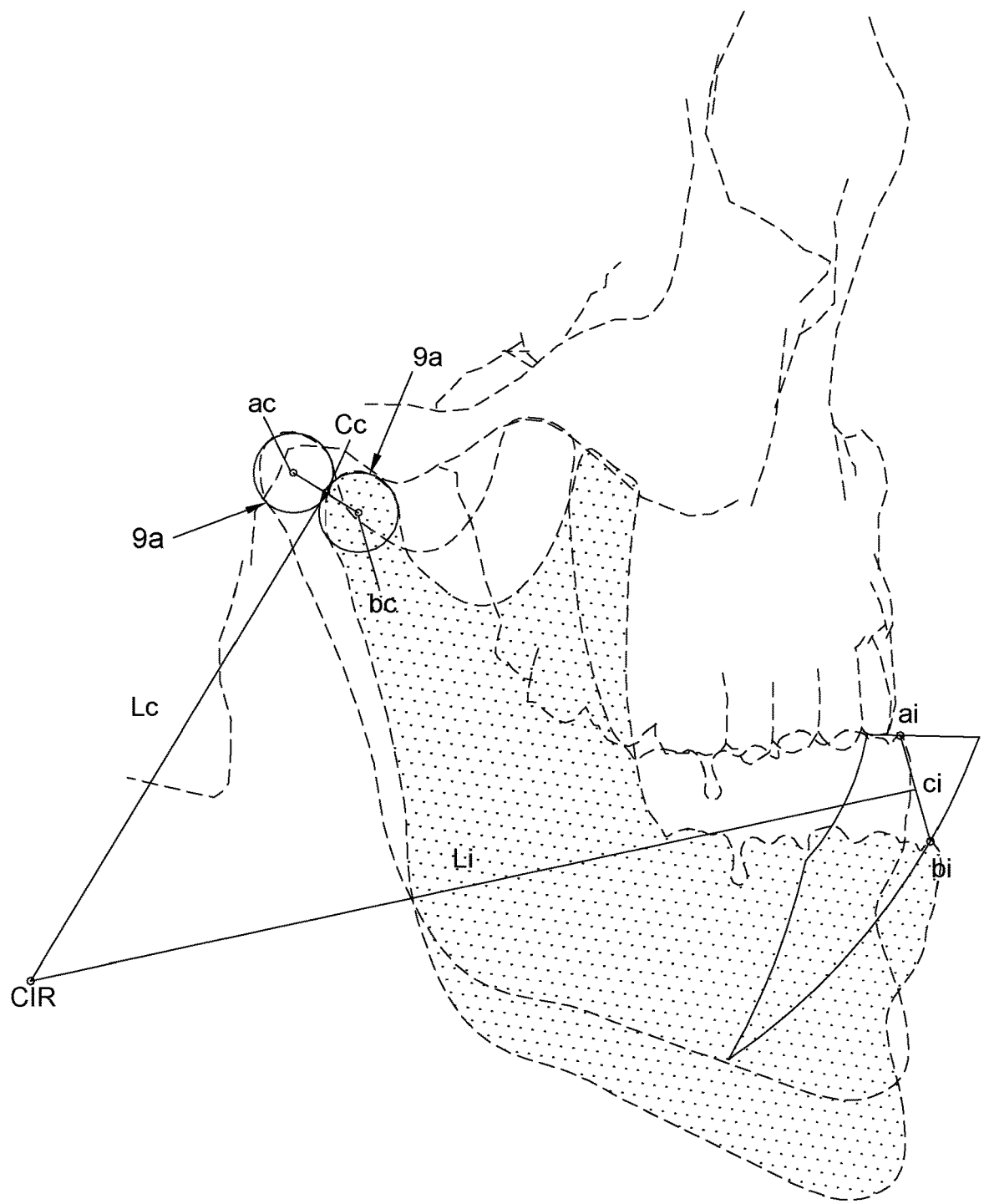

In the equation described, the point "bl" on the contact surface (3a) has been calculated from the angle "α" as shown in FIGS. 11 and 12, for example.

Figure 12A:
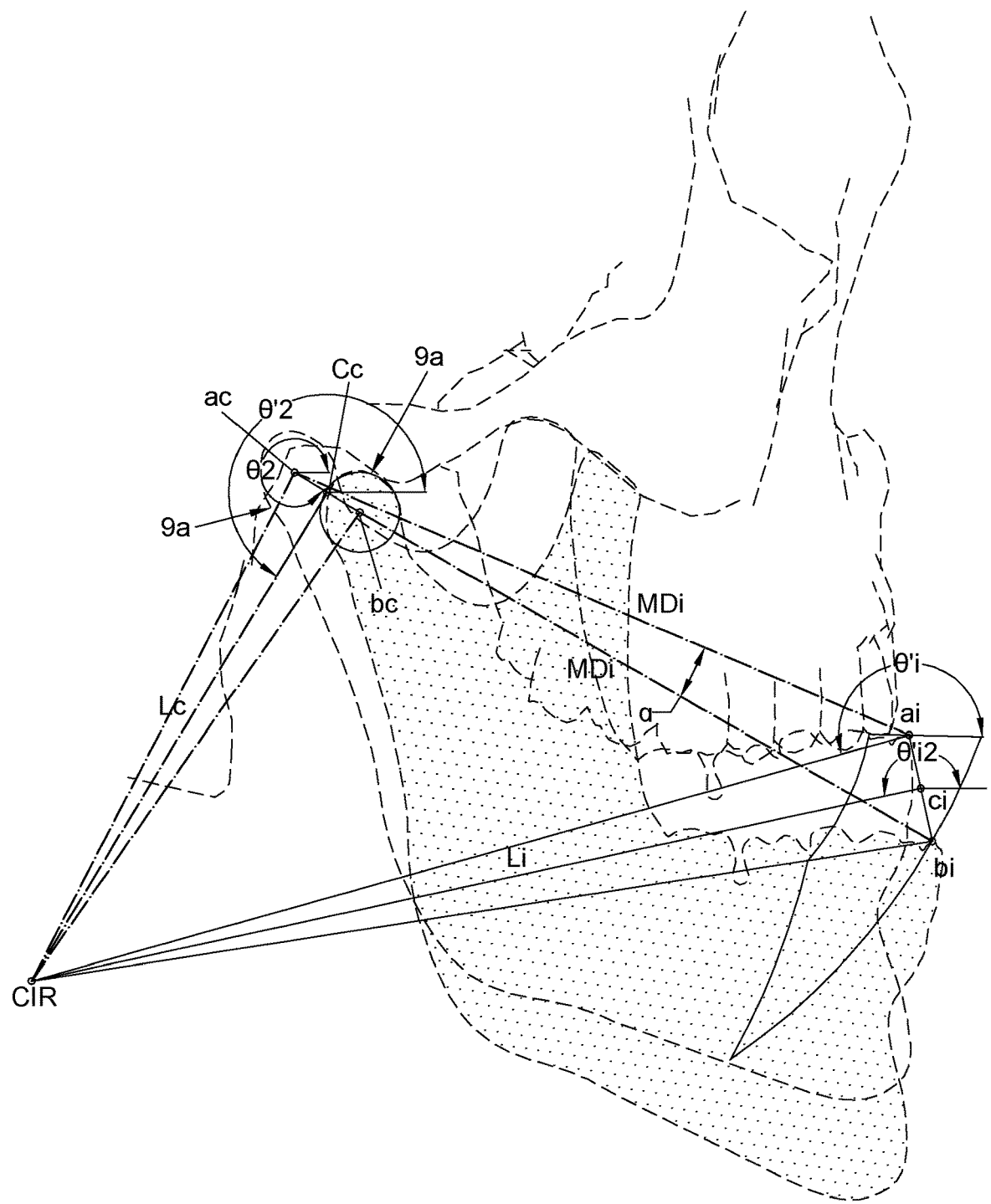
Figure 13:
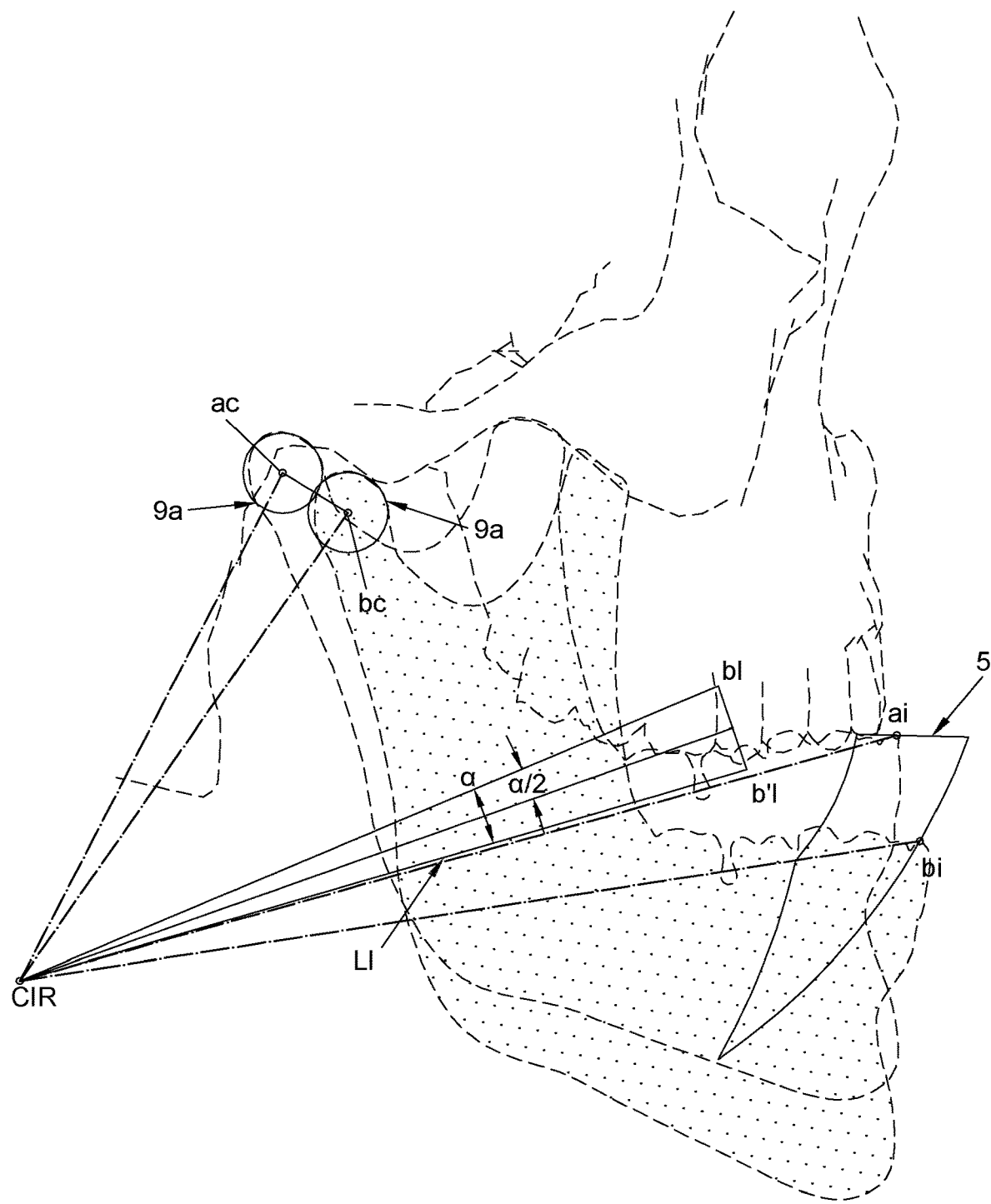

Said point "bl" of the contact surface (3a) can also be calculated from the intersection in the "ICR" point of two straight lines "Lc" and "Li" which are perpendicular, respectively to two lines: a first line which links the positions "ai", "bi" of the point (p) of the lower incisors with the mouth closed and open; and a second line linking the positions "ac", "bc" from the centre of the condyle (9a) that also correspond with the mouth closed and with the mouth open. The two straight lines "Lc" and "Li" are linked to a central points "ci", "cc" of the first and second line, respectively; all as shown in FIGS. 12 and 12a.

wherein:

$x_{ICR}=x_{cc}+L_c \cdot \cos(\theta_2')$ $y_{ICR}=y_{cc}+L_c \cdot \sin(\theta_2')$ wherein:

$\theta_2'=\theta_2-90$ $x_{cc}+L_c \cdot \cos(\theta_2')=x_{ci}+L_i \cdot \cos(\theta_{i2}')$ $y_{cc}+L_c \cdot \sin(\theta_2')=y_{ci}+L_i \cdot \sin(\theta_{i2}')$ $L_c$ and $L_i$ are obtained wherein:

cc=($x_{cc}$, $y_{cc}$)=middle point of the straight line ac-bc;
ci=($x_{ci}$, $y_{ci}$)=middle point of the straight line ai-bi;

$$\theta_2 = \tan^{-1}\left(\frac{y_{bc}-y_{ac}}{x_{bc}-x_{ac}}\right)$$

$$\theta_{i2}' = \theta_i - 90$$

wherein:

$$\theta_i = \tan^{-1}\left(\frac{y_{bi}-y_{ai}}{x_{bi}-x_{ai}}\right)$$

$$x_{ac} = x_{ai} + DM_i \cdot \cos(\theta_1)$$

$$y_{ac} = y_{ai} + DM_i \cdot \sin(\theta_1)$$

$$x_{bc} = x_{bi} + DM_i \cdot \cos(\theta_1')$$

$$y_{bc} = y_{bi} + DM_i \cdot \sin(\theta_1')$$

wherein:

$\theta_1'=\theta_1-90$ ai=($x_{ai}$, $y_{ai}$)=known input datum;
bi=($x_{bi}$, $y_{bi}$)=known input datum;

It should be noted that the angles shown (FIG. 13a) are measured between parallel planes to the plane of occlusion (6) with the patient's mouth closed and with respect to the first and second-line linking, respectively, the two positions "ai", "bi" of the point (p) of the incisors and the two positions "ac", "bc" of the centre of the condyle (9a).

Figure 14A:
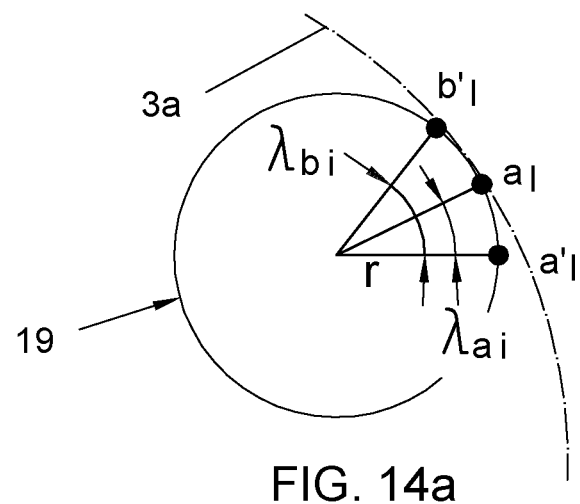
Figure 14B:
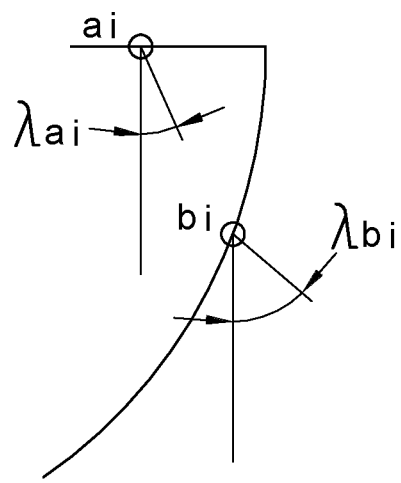

In particular, a way to calculate the contact surface (3a) in the upper splint (1) mounted on the upper jaw (16) of the patient, begins with, for example, a follower (19) having a circular section and that obviously will contact on the contact surface (3a) during use of the device of the invention, so that the references that are indicated in FIGS. 14a and 14b relate to the following elements.

r: radius of the follower (19).

$\lambda_{ai}$: Angle which will begin from the contact surface (3a) which corresponds to the initial position (ai) of the point (p) of the lower incisors (7) of the lower jaw (9); this angle having a value between 0 and 90°.

$\lambda_{bi}$: Angle which will reach the contact surface (3a) up to a position which corresponds to the final position (bi) of the point (p) of the lower incisors (7) of the lower jaw (9); this angle having a value between 0 and 90°.

$a_l'$: known precise location of the follower (19) as being input data.

$a_l$: corresponding lower point with the tangential contact of the follower (19) and contact surface (3a).

$b_l$: Reference point corresponding to another area of tangential contact of the follower (19) and contact surface (3a).

wherein $x_{al}=x_{al}'+r \cdot (1-\cos(\lambda_{ai}))$;

$y_{al}=y_{al}'\cdot r \cdot \sin(\lambda_{ai})$;

$x_{bl}=x_{ICR}+L_l \cdot \cos(\theta_4)$;

$y_{bl}=y_{ICR}+L_l \cdot \sin(\theta_4)$;

wherein:
ICR=($x_{ICR}$, $y_{ICR}$) being calculated by one of the two above mentioned possible options, i.e.:

$x_{ICR}=x_{cc}+L_c\cdot\cos(\theta_2')$ $y_{ICR}=y_{cc}+L_c\cdot\sin(\theta_2')$ or $x_{ICR}=X_{ai}+L_{ciri}\cos(\theta_i')$;

$y_{ICR}=y_{ai}+L_{ciri}\sin(\theta_i')$;

wherein $L_l=\sqrt{(x_{b1}'-x_{ICR})^2+(y_{b1}'-y_{ICR})^2}$;

$\theta_4=\theta_3+\alpha$;

wherein $x_{bl'} = x_{al}' + r\cdot(1-\cos(\lambda_{bi}))$;

$y_{bl'} = y_{al}' + r\cdot\sin(\lambda_{bi})$;

$\theta_3 = \tan^{-1}\left(\dfrac{y_{ICR}-y_{bl}'}{x_{ICR}-x_{bl}'}\right)$;

$\alpha = \theta_1 - \theta_1'$

Figures 15A, 15B, 15C, 15D, 15E:
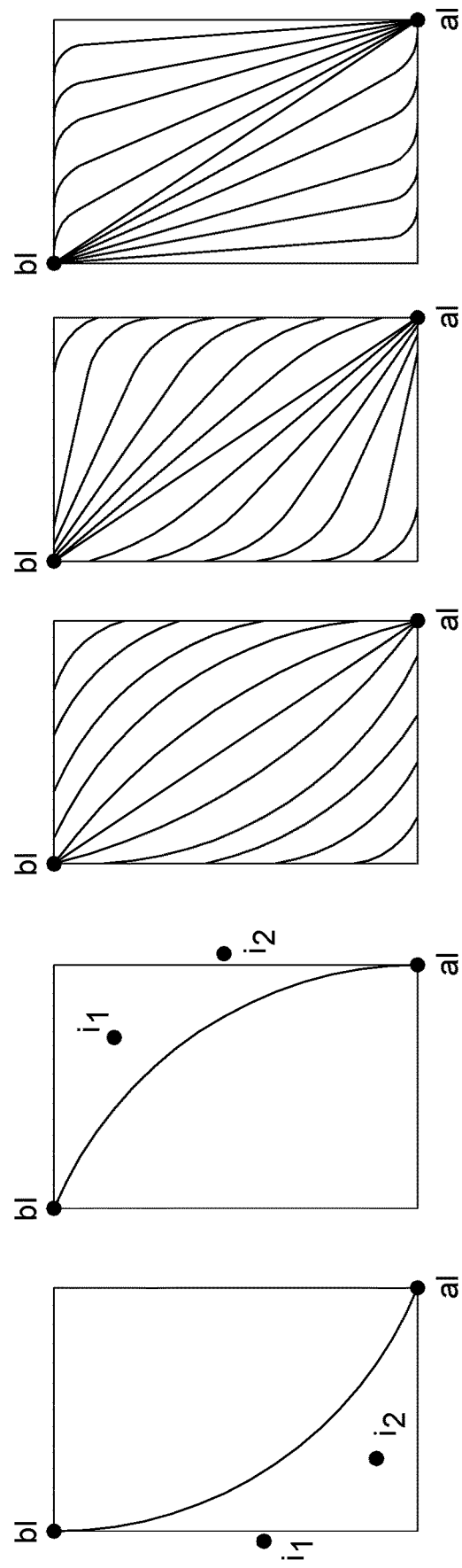
FIGS. 15a and 15b show two different embodiments of two curved trajectories that define two contact surfaces when the followers are placed in the upper splint and the contact surfaces in the lower splint.
FIGS. 15c to 15e show possible multiple curved trajectories of the contact surface, wherein said curved trajectories are defined by the equation described.

In FIGS. 15a and 15b are two different embodiments of two curved trajectories that define two contact surfaces (3a), each of which includes the initial point (a1) and the final point (b1). In these two FIGS. 15a and 15b other points (i1), and (i2) are also shown, whose coordinates are used to calculate other additional points of the curved trajectories defined by the equation described; wherein said additional points have coordinates $(x_{i1}, y_{i1})$, $(x_{i2}, y_{i2})$.

Figure 16A:
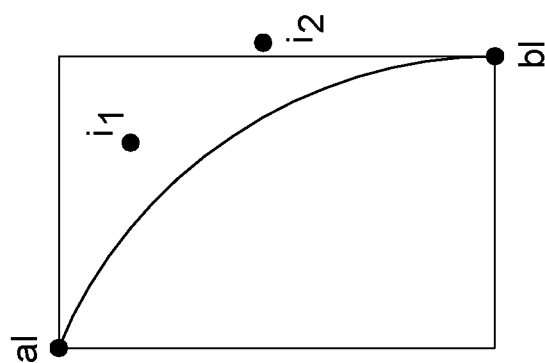
FIGS. 16a and 16b show two different embodiments of two curved trajectories that define two contact surfaces when the followers are placed in the lower splint and the contact surfaces in the upper splint.
Figure 16B:
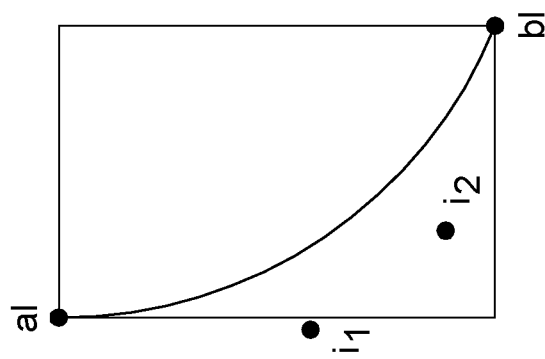

In case the contact surface (3a) were part of the upper splint (1) and the follower (19) were part of the lower splint (2), the curved trajectories obtained would be the mirror ones of those depicted in FIGS. 15a and 15b; i.e., FIGS. 16a and 16b.

Finally, in the FIGS. 15c to 15e multiple curved trajectories possible of the contact surface (3a) are shown, wherein said curved trajectories are defined by the equation described.

The invention claimed is:

1. An intra-oral device for mandibular adjustment, comprising:
 an upper splint configured to adapt to an upper jaw of a patient and a lower splint configured to adapt to a lower jaw of said patient;
 at least one follower and at least one contact surface on which the follower contacts;
 wherein the upper splint and lower splint interact with each other through the follower and the contact surface; and wherein the lower jaw is placeable in different positions with respect to the upper jaw;
 wherein the contact surface is defined by a curve according to the equation:

$X=X_1+X_2+X_3+X_4$;

$Y=Y_1+Y_2+Y_3+Y_4$;

wherein:

$X_1=x_{ai'}(1-t)^3$;

$X_2=3\cdot x_{i1}\cdot t\cdot(1-t)^2$;

$X_3=3\cdot x_{i2}\cdot t^2\cdot(1-t)$;

$X_4=x_{bl'}\cdot t^3$;

$Y_1=y_{ai'}(1-t)^3$;

$Y_2=3\cdot y_{i1}\cdot t\cdot(1-t)^2$;

$Y_3=3\cdot y_{i2}\cdot t^2\cdot(1-t)$;

$Y_4=Y_{bl'}\cdot t^3$;

wherein:

$x_{bl}=x_{ICR}+L_l\cos(\theta_4)$;

$y_{bl}=y_{ICR}+L_l\sin(\theta_4)$;

a1=$(x_{al},y_{al})$=known input datum;
wherein:

$L_l=\sqrt{(x_{a1}-x_{ICR})^2+(y_{a1}-y_{ICR})^2}$;

$x_{ICR}=X_{ai}+L_{ciri}\cos(\theta_i')$;

$y_{ICR}=y_{ai}+L_{ciri}\sin(\theta_i')$;

$\theta_4=\theta_3+\alpha$;

wherein:

$L_{ciri} = \dfrac{l_i}{\sin\left(\dfrac{\alpha}{2}\right)}$ $\theta_i' = \theta_i - 90 + \dfrac{\alpha}{2}$ $\theta_3 = \arctan\left(\dfrac{y_{ICR}-y_{al}}{x_{ICR}-x_{al}}\right)$ wherein:
 $l_i$=known lineal distance measured to the middle point of the straight line ai-bi;
 $\theta_i$=known angle that forms the straight line ai-bi;
wherein:

$\theta_i = \tan^{-1}\left(\dfrac{y_{bi}-y_{ai}}{x_{bi}-x_{ai}}\right)$

α=angle of rotation of the jaw;
wherein:

$\alpha=\theta_1-\theta_1'$;

wherein:

$x_{ai}+MDi\cdot\cos(\theta_1)=x_{bi}+x_{bc}+s\cdot\cos(\beta)$;

$y_{ai}+MDi\cdot\sin(\theta_1)=y_{bi}+y_{bc}+s\cdot\sin(\beta)$;

$\theta_1$ and s are obtained;
wherein:
 ai=$(x_{ai},y_{ai})$=known input datum;
 bi=$(x_{bi},y_{bi})$=known input datum;
 bc=$(x_{bc},ydbc)$=known datum;
 MDi=mandibular distance known;
 β=known angle;
 wherein:
  the variable "t" is delimited between 0 and 1;
  the coordinates "$x_{al}$", "$y_{al}$" define an initial point "a1" of the contact surface corresponding to a known initial position of the follower when the mouth of the patient is closed;

the coordinates "$x_{bl}$", "$y_{bl}$" define a final point "bl" of the contact surface which corresponds to a final position of the follower with the patient's mouth open;

the variables "$x_{i1}$", "$x_{i2}$" have a value delimited between the coordinates "$x_{al}$" and "$x_{bl}$"; and the variables "$y_{i1}$", "$y_{i2}$" have a value delimited between the coordinates "$y_{al}$" and "$y_{bl}$";

"ICR" is a point corresponding to an instantaneous centre of rotation of the lower jaw;

"$L_l$" is the distance between the point "ICR" and the initial point "al" of the contact surface;

"$L_{ciri}$" is the distance between the point "ICR" and a position "ai" of a point of the lower incisors of the lower jaw with the mouth closed;

the angle "$\theta_4$" comprises a delimited angular space between a plane parallel to the plane of occlusion with the mouth of the patient closed, and a direction passing through the point "ICR" and the final point "bl" of the contact surface;

the angle "$\theta_3$" comprises a delimited angular space between a plane parallel to the plane of occlusion with the mouth of the patient closed, and a direction passing through the point "ICR" and the initial point "al" of the contact surface;

the angle "$\theta'_i$" comprises an angular space delimited between the plane of occlusion with the mouth of the patient closed and a direction passing through the point "ICR" and the position "ai" of the point of the lower incisors of the lower jaw with the mouth of the patient closed;

the angle "$\theta_i$" comprises an angular space delimited between the plane of occlusion with the mouth of the patient closed, and a direction passing through position "ai" of the point of the lower incisors of the lower jaw with the mouth closed and through a position "bi" of the point of the lower incisors of the lower jaw when the mouth of the patient is open;

the angle "$\alpha$" comprises an angular space delimited between a first direction passing through the position "ai" of the point of the lower incisors of the lower jaw and an initial point "ac" of the condyle with the mouth of the patient closed, and a second direction passing through said point "ac" and a final point "bc" of the condyle with the mouth of the patient open; wherein the angle "$\alpha$" is an angular amplitude corresponding to the rotation of the lower jaw when the point of the lower incisors passes from the position "ai" to the position "bi";

the angle "$\beta$" comprises a delimited angular space between a plane parallel to the plane of occlusion with the mouth of the patient closed, and a direction passing through the initial point "ac" of the condyle with the mouth closed and through the final point "bc" of the condyle with the mouth open;

the "s" distance is a distance delimited between the initial point "ac" of the condyle with the mouth closed and the final point "bc" of the condyle with the patient's mouth open; and "MDi" is the distance between the centre of the condyle and the point of the lower incisors of the lower jaw.

2. The intra-oral device for mandibular adjustment, according to claim 1, wherein:

the intra-oral device comprises extensions, which in turn comprise two side contact surfaces and two side followers, which consist of lugs protruding outwardly with respect to opposite outer faces selected from opposite outer faces of the lower splint and opposite outer faces of the upper splint;

the side followers are located in an area selected between an area located below a plane delimiting a lower surface of the upper splint and an area located above a plane delimiting an upper surface of the lower splint;

the contact surfaces are located in extensions; and wherein the contact surfaces in combination with the followers constitute a means for guiding and positioning of the lower jaw when the followers are in tangential contact with the contact surfaces.

3. The intra-oral device for mandibular adjustment, according to claim 2, wherein the upper splint and the lower splint are related by a coupling with lateral gaps; wherein said lateral gaps are delimited between the extensions, and portions of the opposite outer faces of the lower splint or upper splint; and wherein said lateral gaps allow controlled lateral mobility in a transverse direction of the lower jaw towards two opposite sides of said lower jaw when the patient makes use of the device.

4. The intra-oral device for mandibular adjustment, according to claim 2, wherein the extensions include inner faces and outer faces opposite to the inner faces; wherein said outer faces comprise dome-shaped surfaces.

5. The intra-oral device for mandibular adjustment, according to claim 2, wherein the contact surfaces in combination with the followers constitute static positioning means of the lower jaw if the patient's mouth is closed when the followers are in tangential contact with the contact surfaces.

6. The intra-oral device for mandibular adjustment, according to claim 4, wherein the extensions include housings delimited by edges comprising the contact surfaces; wherein the followers are fitted into the housings.

7. The intra-oral device for mandibular adjustment, according to claim 6, wherein the side followers include ends located inside the housings without protruding outwardly with respect to the outer faces of the extensions.

8. The intra-oral device for mandibular adjustment, according to claim 6, wherein each housing comprises a closed contour that is formed by a lower stop, the contact surface, an additional surface facing said contact surface, and an upper stop that is configured to be able to adjust the height of the housing according to optimum opening of the mouth of the patient.

9. The intra-oral device for mandibular adjustment, according to claim 8, wherein the two side contact surfaces are contained in two asymmetrical planes; wherein said contact surfaces are defined by different curves.

10. The intra-oral device for mandibular adjustment, according to claim 8, wherein:

the followers are in contact with the contact surfaces, with the upper stops and the lower stops of the housings; wherein said described configuration maintains a static position of the lower splint with respect to the upper splint; and wherein the device maintains the lower jaw in a resting position with the patient's mouth closed blocking the mobility of the lower jaw.

11. The intra-oral device for mandibular adjustment, according to claim 8, wherein each of the contact surfaces comprises a profile with arched trajectory.

* * * * *

UNITED STATES PATENT AND TRADEMARK OFFICE
CERTIFICATE OF CORRECTION

PATENT NO. : 11,304,844 B2
APPLICATION NO. : 16/619252
DATED : April 19, 2022
INVENTOR(S) : Garcia Reyes et al.

It is certified that error appears in the above-identified patent and that said Letters Patent is hereby corrected as shown below:

In the Claims

Column 21, Line 63, Claim 1, delete "$X_1 = x_{at} \cdot (1-t)^3$;" and insert --$X_1 = x_{al} \cdot (1-t)^3$;--

Column 22, Line 3, Claim 1, delete "$Y_1 = y_{at} \cdot (1-t)^3$;" and insert --$Y_1 = y_{al} \cdot (1-t)^3$;--

Column 22, Line 20, Claim 1, delete "$x_{ICR} = X_{al} + L_{ciri} \cdot \cos(\theta_i')$;" and insert --$x_{ICR} = x_{ai} + L_{ciri} \cdot \cos(\theta_i')$;--

Column 22, Line 59, Claim 1, delete "($x_{bc}$,ydbc)" and insert --$(x_{bc}, y_{bc})$--

Signed and Sealed this
Nineteenth Day of July, 2022

Katherine Kelly Vidal
*Director of the United States Patent and Trademark Office*